US011166721B2

(12) United States Patent
Campbell et al.

(10) Patent No.: US 11,166,721 B2
(45) Date of Patent: Nov. 9, 2021

(54) STAPLE RETAINER FOR SURGICAL STAPLER CARTRIDGE

(71) Applicant: Ethicon LLC, Guaynabo, PR (US)

(72) Inventors: Macall K. Campbell, Brentwood, TN (US); Daniel L. Baber, West Chester, OH (US)

(73) Assignee: Cilag GmbH International, Zug (CH)

( * ) Notice: Subject to any disclaimer, the term of this patent is extended or adjusted under 35 U.S.C. 154(b) by 190 days.

(21) Appl. No.: 16/395,364

(22) Filed: Apr. 26, 2019

(65) Prior Publication Data
US 2020/0337701 A1  Oct. 29, 2020

(51) Int. Cl.
*A61B 17/072* (2006.01)
*A61B 17/00* (2006.01)

(52) U.S. Cl.
CPC ............. *A61B 17/07207* (2013.01); *A61B 2017/00477* (2013.01); *A61B 2017/0725* (2013.01); *A61B 2017/07257* (2013.01); *A61B 2017/07264* (2013.01); *A61B 2017/07271* (2013.01); *A61B 2017/07285* (2013.01)

(58) Field of Classification Search
CPC .... A61B 17/07207; A61B 2017/00477; A61B 2017/0725; A61B 2017/07257; A61B 2017/07264; A61B 2017/07271; A61B 2017/07285
See application file for complete search history.

(56) References Cited

U.S. PATENT DOCUMENTS 3,315,863 A * 4/1967 O'Dea ................. A61B 17/072
227/19
4,715,520 A * 12/1987 Roehr, Jr. ............ A61B 17/072
227/19
(Continued)

FOREIGN PATENT DOCUMENTS

EP          0488768 A1    6/1992
WO   WO 2012/142872 A1   10/2012

OTHER PUBLICATIONS

Chinese Office Action, Notification of the First Office Action, dated Feb. 28, 2017 for Application No. 2014800108866, 7 pages.
(Continued)

*Primary Examiner* — Nathaniel C Chukwurah
*Assistant Examiner* — Lucas E. A. Palmer
(74) *Attorney, Agent, or Firm* — Frost Brown Todd LLC

(57) ABSTRACT

A staple retainer for a surgical staple cartridge unit includes a body having first and second body sides configured to be positioned within an aperture defined between an anvil and a deck of the cartridge unit such that the first body side confronts the anvil and the second body side confronts the deck. The second body side is configured to retain staples within openings in the deck. A first protrusion at the first body side is configured to contact the anvil at a first location, and a second protrusion at the first body side is configured to contact the anvil at a second location. The protrusions are configured to resiliently deflect toward the second body side in response to the staple retainer being positioned within the (Continued)

aperture, and are further configured to cooperate with the second body side to maintain a predetermined distance between the anvil and the deck.

20 Claims, 29 Drawing Sheets

(56) References Cited

U.S. PATENT DOCUMENTS

| | | | |
|---|---|---|---|
| 4,767,044 A * | 8/1988 | Green | A61B 17/072 227/19 |
| 4,805,823 A | 2/1989 | Rothfuss | |
| 5,275,323 A | 1/1994 | Schulze et al. | |
| 5,307,976 A | 5/1994 | Olson et al. | |
| 5,415,334 A | 5/1995 | Williamson, IV et al. | |
| 5,465,895 A | 11/1995 | Knodel et al. | |
| 5,487,500 A | 1/1996 | Knodel et al. | |
| 5,597,107 A | 1/1997 | Knodel et al. | |
| 5,605,272 A | 2/1997 | Witt et al. | |
| 5,632,432 A | 5/1997 | Schulze et al. | |
| 5,653,373 A | 8/1997 | Green et al. | |
| 5,662,258 A | 9/1997 | Knodel et al. | |
| 5,662,667 A | 9/1997 | Knodel | |
| 5,673,840 A | 10/1997 | Schulze et al. | |
| 5,697,543 A | 12/1997 | Burdorff | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,878,938 A | 3/1999 | Bittner et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 6,988,649 B2 | 1/2006 | Shelton, IV et al. | |
| 6,988,650 B2 | 1/2006 | Schwemberger et al. | |
| 7,000,818 B2 | 2/2006 | Shelton, IV et al. | |
| 7,044,352 B2 | 5/2006 | Shelton, IV et al. | |
| 7,083,075 B2 | 8/2006 | Swayze et al. | |
| 7,134,587 B2 | 11/2006 | Schwemberger et al. | |
| 7,143,923 B2 | 12/2006 | Shelton, IV et al. | |
| 7,143,926 B2 | 12/2006 | Shelton, IV et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,303,108 B2 | 12/2007 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,419,080 B2 | 9/2008 | Smith et al. | |
| 7,434,715 B2 | 10/2008 | Shelton, IV et al. | |
| 7,455,208 B2 | 11/2008 | Wales et al. | |
| 7,490,749 B2 | 2/2009 | Schall et al. | |
| 7,524,320 B2 | 4/2009 | Tierney et al. | |
| 7,549,564 B2 | 6/2009 | Boudreaux | |
| 7,644,848 B2 | 1/2010 | Swayze et al. | |
| 7,658,311 B2 | 2/2010 | Boudreaux | |
| 7,691,098 B2 | 4/2010 | Wallace et al. | |
| 7,721,930 B2 | 5/2010 | McKenna et al. | |
| 7,753,245 B2 | 7/2010 | Boudreaux et al. | |
| 7,798,386 B2 | 9/2010 | Schall et al. | |
| 7,806,891 B2 | 10/2010 | Nowlin et al. | |
| 7,954,684 B2 | 6/2011 | Boudreaux | |
| 8,210,411 B2 | 7/2012 | Yates et al. | |
| 8,245,898 B2 | 8/2012 | Smith et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,579,176 B2 | 11/2013 | Smith et al. | |
| 8,602,288 B2 | 12/2013 | Shelton, IV et al. | |
| 8,608,046 B2 | 12/2013 | Laurent et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 9,186,142 B2 | 11/2015 | Fanelli et al. | |
| 9,517,065 B2 | 12/2016 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,867,615 B2 | 1/2018 | Fanelli et al. | |
| 10,045,780 B2 | 8/2018 | Adams et al. | |
| 10,092,292 B2 | 10/2018 | Boudreaux et al. | |
| 2002/0020732 A1* | 2/2002 | Adams | A61B 17/072 227/180.1 |
| 2005/0023324 A1 | 2/2005 | Doll et al. | |
| 2005/0139629 A1* | 6/2005 | Schwemberger | A61B 17/072 227/19 |
| 2005/0139633 A1* | 6/2005 | Wukusick | A61B 17/072 227/176.1 |
| 2005/0139636 A1* | 6/2005 | Schwemberger | A61B 17/072 227/180.1 |
| 2006/0180634 A1 | 8/2006 | Shelton, IV et al. | |
| 2007/0010838 A1 | 1/2007 | Shelton, IV et al. | |
| 2007/0073341 A1 | 3/2007 | Smith et al. | |
| 2007/0084897 A1 | 4/2007 | Shelton, IV et al. | |
| 2007/0175955 A1 | 8/2007 | Shelton, IV et al. | |
| 2008/0099530 A1 | 5/2008 | Olson et al. | |
| 2010/0193567 A1 | 8/2010 | Scheib et al. | |
| 2011/0084112 A1 | 4/2011 | Kostrzewski | |
| 2011/0163147 A1 | 7/2011 | Laurent et al. | |
| 2011/0290853 A1 | 12/2011 | Shelton, IV et al. | |
| 2012/0132663 A1* | 5/2012 | Kasvikis | A61B 17/07207 220/694 |
| 2012/0138660 A1 | 6/2012 | Shelton, IV | |
| 2012/0145714 A1* | 6/2012 | Farascioni | A61B 50/30 220/260 |
| 2012/0181322 A1 | 7/2012 | Whitman et al. | |
| 2012/0199630 A1 | 8/2012 | Shelton, IV | |
| 2012/0199632 A1 | 8/2012 | Spivey et al. | |
| 2012/0203247 A1 | 8/2012 | Shelton, IV et al. | |
| 2013/0012957 A1 | 1/2013 | Shelton, IV et al. | |
| 2014/0224686 A1* | 8/2014 | Aronhalt | A61B 17/0682 206/339 |
| 2016/0000428 A1* | 1/2016 | Scirica | A61B 1/00089 227/180.1 |
| 2016/0278764 A1* | 9/2016 | Shelton, IV | A61L 24/046 |
| 2016/0278775 A1* | 9/2016 | Shelton, IV | A61B 17/105 |
| 2018/0168648 A1* | 6/2018 | Shelton, IV | A61B 34/30 |
| 2020/0261088 A1* | 8/2020 | Harris | A61B 50/20 |

OTHER PUBLICATIONS

Extended European Search Report dated May 16, 2014 for Application No. 14157358.
Extended European Search Report and Written Opinion dated Nov. 8, 2016 for Application No. EP 16176672.0, 8 pages.
International Search Report and Written Opinion dated May 27, 2014 for International Application No. PCT/US2014/016202, 6 pages.
International Preliminary Report on Patentability dated Sep. 1, 2015 for International Application No. PCT/US2014/016202, 9 pages.
U.S. Appl. No. 16/234,740, entitled "Surgical Stapler with Sloped Staple Deck for Varying Tissue Compression," filed Dec. 28, 2018.
U.S. Appl. No. 16/395,357, entitled "Tissue Cutting Washer for Right Angle Surgical Stapler," filed Apr. 26, 2019.
U.S. Appl. No. 16/395,359, entitled "Cartridge Based Lockout Mechanism for Right Angle Surgical Stapler," filed Apr. 26, 2019.
U.S. Appl. No. 16/395,364, entitled "Staple Retainer for Surgical Stapler Cartridge," filed Apr. 26, 2019.
U.S. Appl. No. 16/583,690, entitled "Circular Surgical Stapler," filed Sep. 26, 2019.

(56) References Cited

OTHER PUBLICATIONS

Design U.S. Appl. No. 29/689,028, entitled "Staple Retainer for Surgical Stapler Cartridge," filed Apr. 26, 2019.
European Search Report and Written Opinion dated Jul. 7, 2020 for Application No. EP 20171322.9, 8 pgs.
International Search Report and Written Opinion dated Jun. 29, 2020 for Application No. PCT/IB2020/053516, 10 pgs.

* cited by examiner

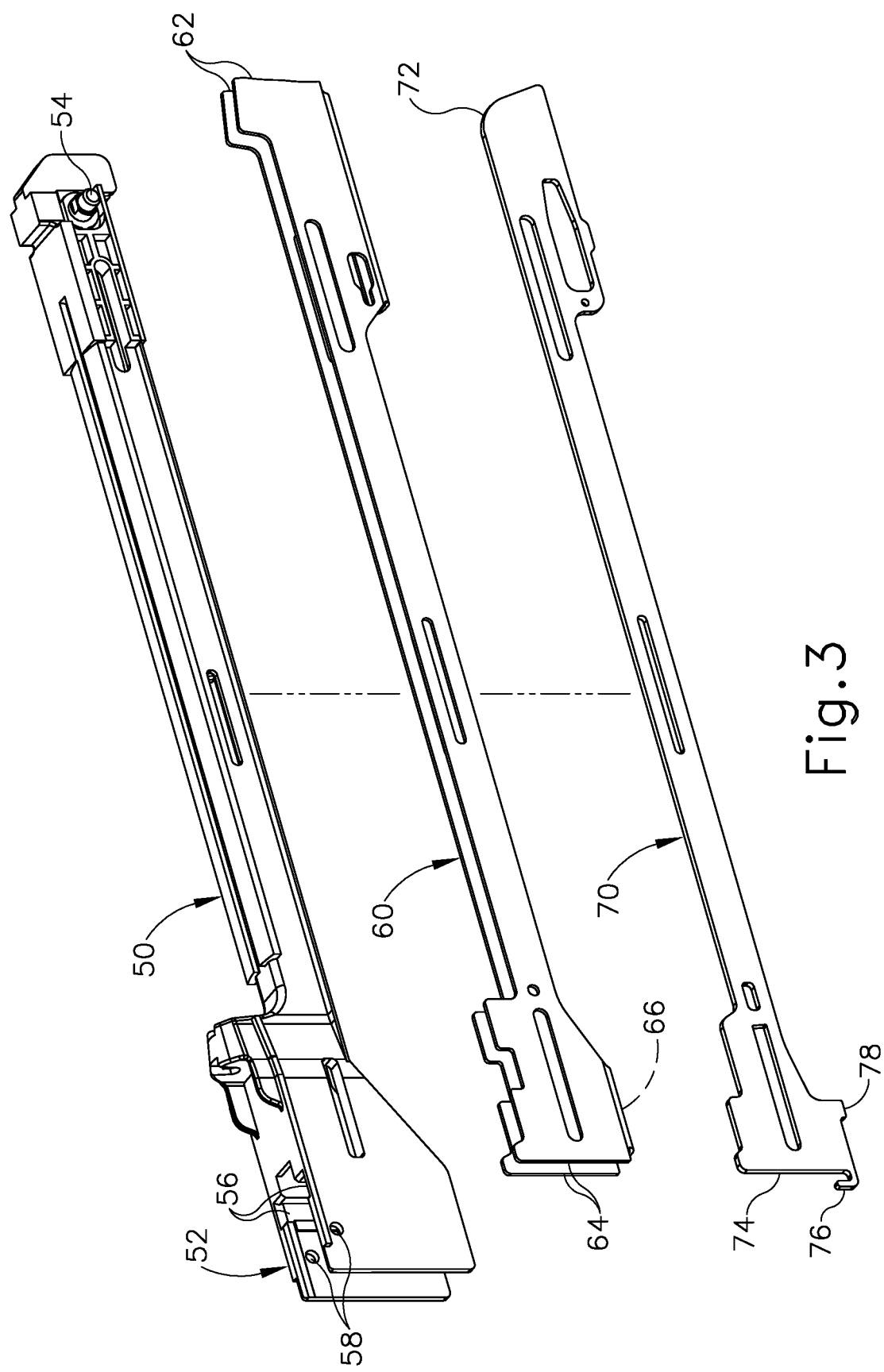

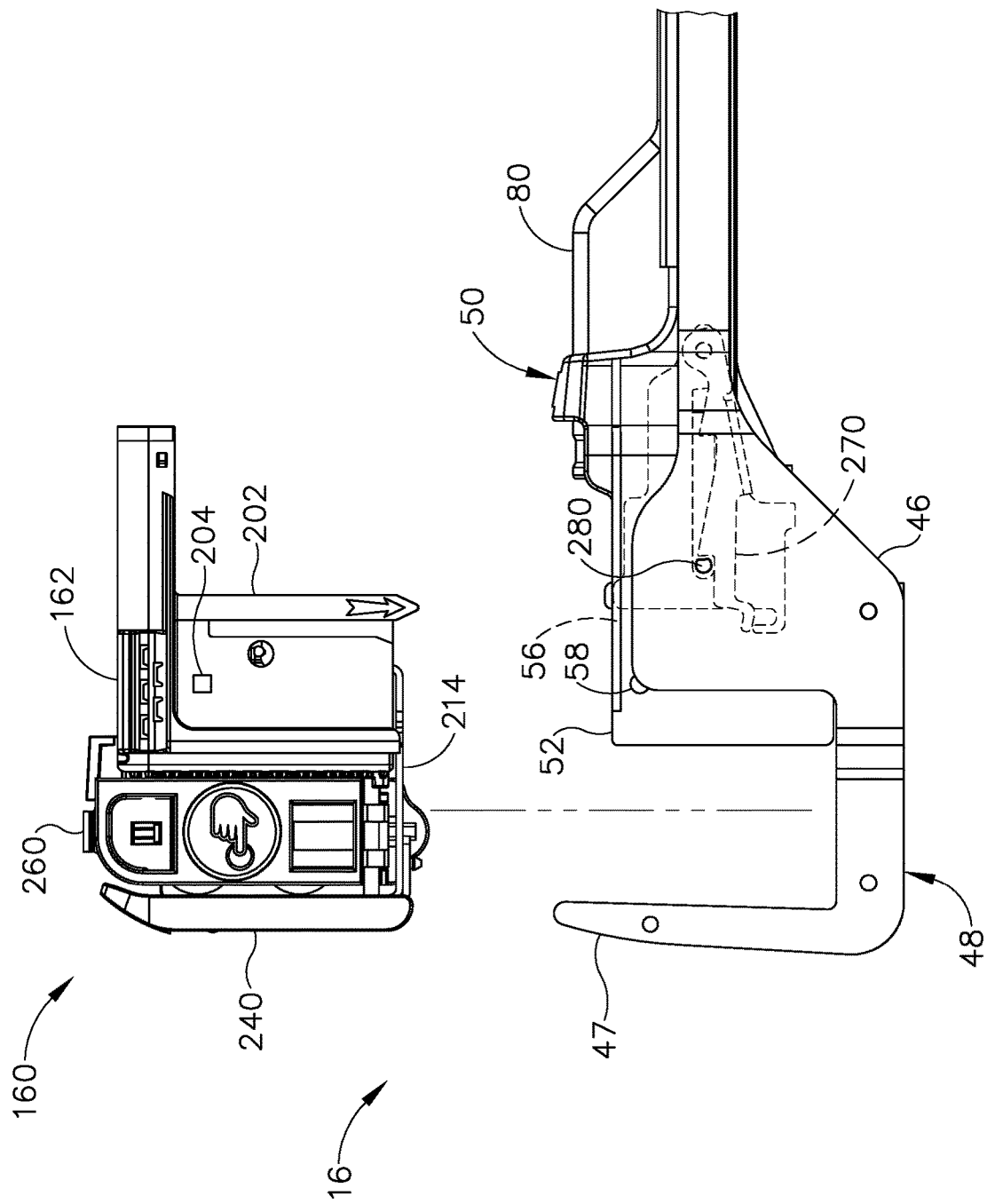

STAPLE RETAINER FOR SURGICAL STAPLER CARTRIDGE

BACKGROUND

Some surgical staplers are operable to clamp down on one or more layers of patient tissue, form staples through the layers of tissue to substantially seal the layers of tissue together near the formed staples, and cut through the layers of clamped tissue for forming severed ends of operatively sealed tissue. An exemplary stapling instrument includes a pair of cooperating elongate jaw members, where each jaw member is adapted to be inserted into a patient and positioned relative to tissue that is to be stapled. One of the jaw members supports a staple cartridge having at least two laterally spaced rows of staples contained therein, and the other jaw member supports an anvil having staple-forming pockets configured to align with the rows of staples in the staple cartridge. Generally, the stapling instrument further includes one or more pusher bars that are actuatable relative to the jaw members to drive staples from the staple cartridge, through tissue clamped between the jaw members, and against the anvil for forming, and also to drive a knife member through the clamped tissue and thereby cut the tissue simultaneously with or subsequent to the stapling. In this manner, the stapling instrument is operable to form a plurality of laterally spaced rows of deformed staples in the clamped tissue, where such rows may comprise linear rows and/or arcuate rows. The knife blade may cut the tissue along a linear or arcuate path that extends between adjacent rows of the staples formed in the clamped tissue.

Merely exemplary surgical staplers are disclosed in U.S. Pat. No. 5,605,272, entitled "Trigger Mechanism for Surgical Instruments," issued Feb. 25, 1997; U.S. Pat. No. 5,697,543, entitled "Linear Stapler with Improved Firing Stroke," issued Dec. 16, 1997; U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007; and U.S. Pat. No. 10,045,780, entitled "Method of Applying Staples in Lower Anterior Bowel Resection," issued Aug. 14, 2018. The disclosure of each of the above-cited U.S. patents and U.S. patent publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3 depicts a disassembled perspective view of actuatable components of the shaft assembly of the surgical stapler of FIG. 1A, including a closure bar of the closure system, a staple bar of the firing system, and a knife bar of the firing system;

FIG. 9A depicts a side elevational view of the end effector of the surgical stapler of FIG. 1A, showing a lockout member of the end effector in a lockout position when a staple cartridge unit is absent from the distal support structure;

Figure 1A:
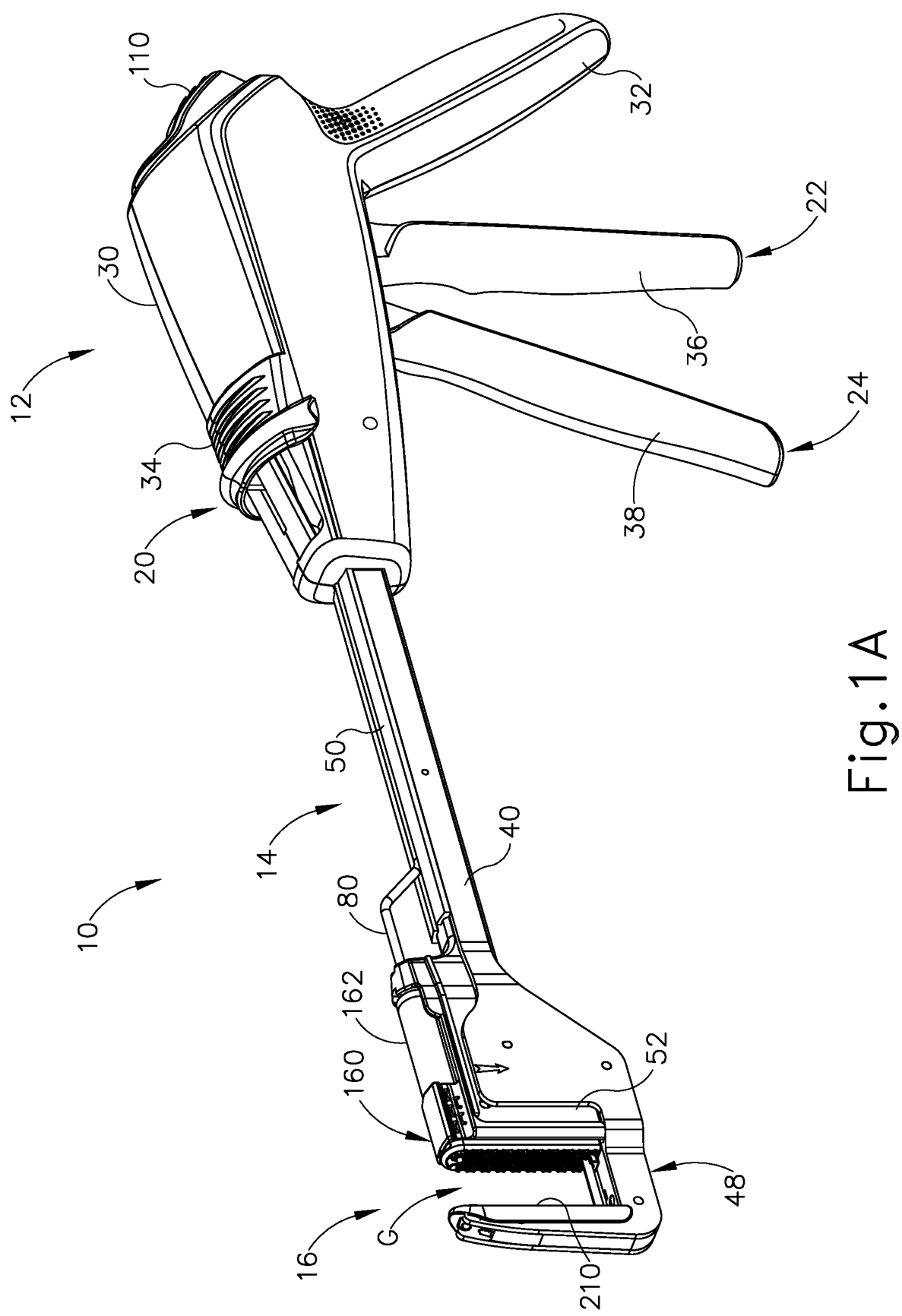
FIG. 1A depicts a perspective view of an exemplary surgical stapler having a handle assembly, a shaft assembly, and an end effector, showing a tissue retaining pin actuation system in a retracted position and the end effector in an open state.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," "left," "right" or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about," "approximately," and the like in connection with any numerical values or ranges of values are intended to encompass the exact value(s) referenced, as well as a suitable dimensional tolerance that enables the referenced feature or combination of features to function for the intended purpose described herein.

I. Overview of Exemplary Right Angle Surgical Stapler

FIG. 1A depicts an exemplary right angle linear surgical stapler (10) that is configured to staple and cut tissue in various non-endoscopic ("open") surgical procedures, including colorectal, thoracic, and bariatric procedures, for example. Right angle linear surgical stapler (10) (also referred to as a "right angle linear cutter") generally includes a handle assembly (12), a shaft assembly (14) extending distally from handle assembly (12), and an end effector (16) at a distal end of shaft assembly (14). As described below, end effector (16) is provided with a "right angle" configuration such that end effector (16) clamps, staples, and cuts tissue in a plane that extends transversely at a right angle to a longitudinal axis defined by shaft assembly (14).

As described in greater detail below, surgical stapler (10) includes several actuation systems for operating end effector (16) via handle assembly (12) during a surgical procedure on a patient. In particular, surgical stapler (10) includes a tissue retaining pin actuation system (20) operable to initially retain tissue within end effector (16); a closure system (22) operable to clamp tissue with end effector (16); and a firing system (24) operable to subsequently staple and cut tissue with end effector (16).

While the teachings herein are shown and described in the context of a "linear" surgical stapler (10) configured to apply linear rows of staples and a linear cut line in tissue, it will be appreciated that any one or more of the teachings herein may be applied to a surgical stapler configured to apply staple rows and a tissue cut line with a non-linear (e.g., curved) configuration, such as a surgical stapler of the type disclosed in any one or more of the references incorporated by reference herein.

A. Handle Assembly and Shaft Assembly of Surgical Stapler

Figure 1B:
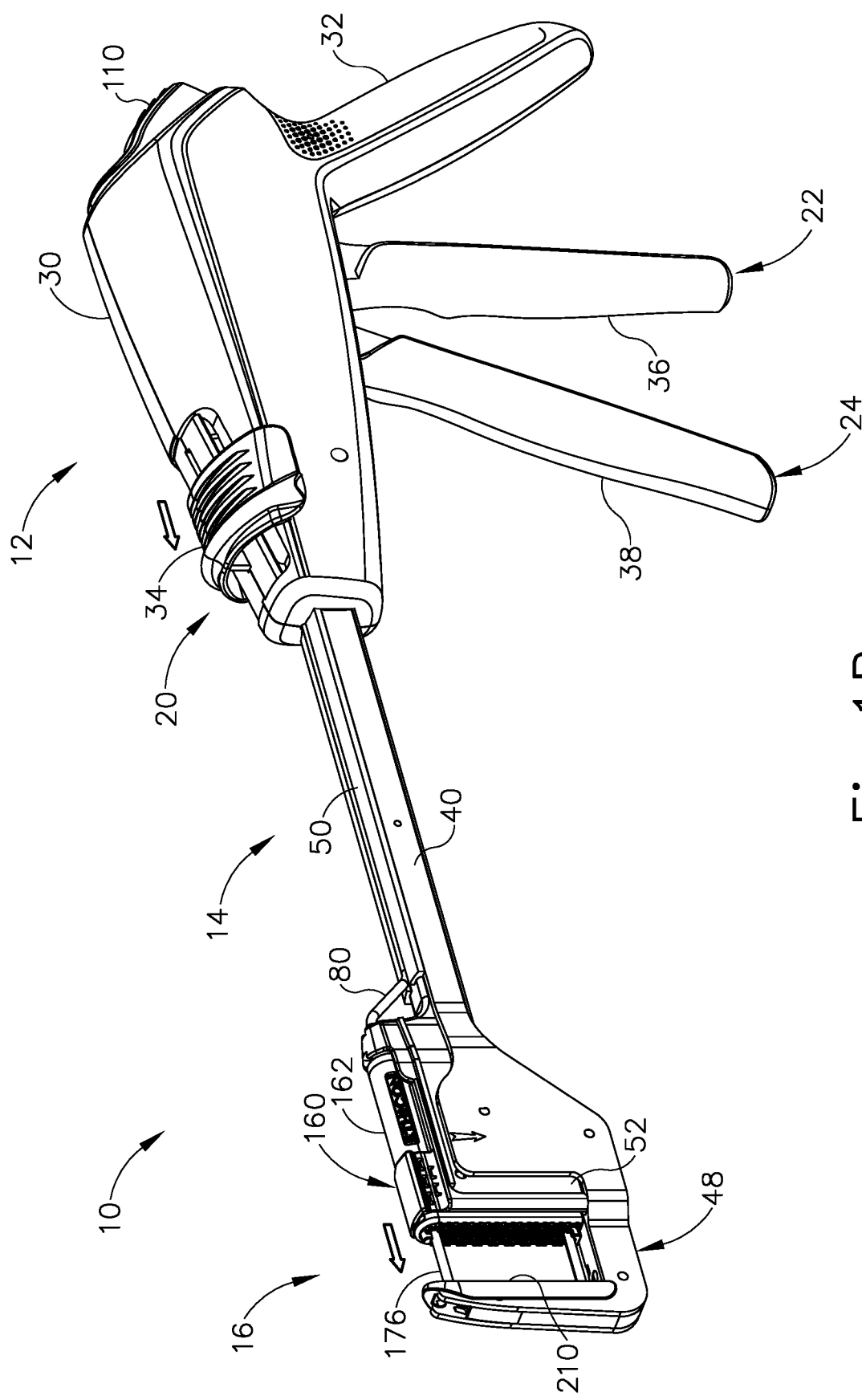
FIG. 1B depicts a perspective view of the surgical stapler of FIG. 1A, showing the tissue retaining pin actuation system in an extended position while the end effector remains in the open state.
Figure 1C:
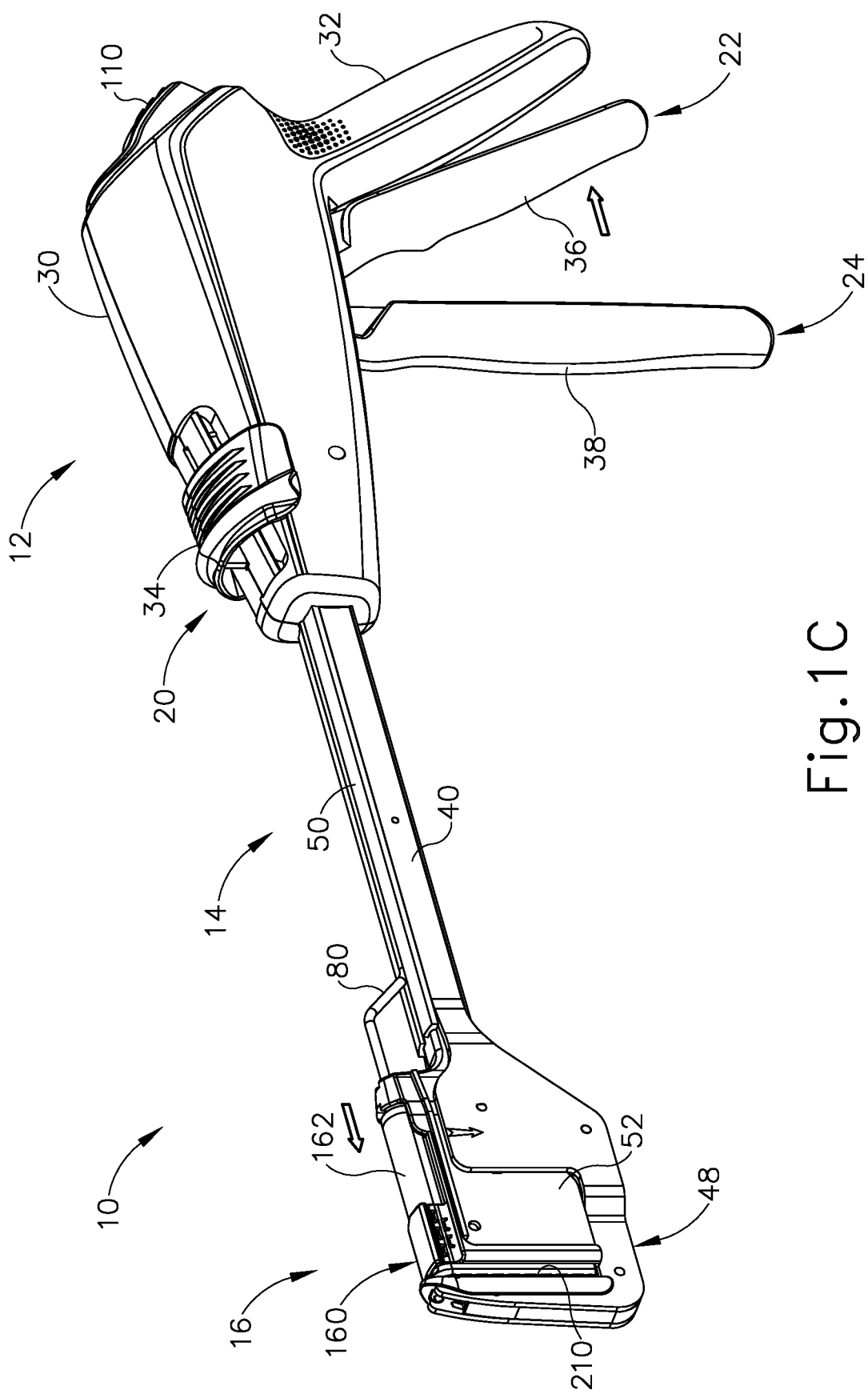
FIG. 1C depicts a perspective view of the surgical stapler of FIG. 1A, showing the end effector in a closed state via actuation of a closure system, while the tissue retaining pin actuation system remains in the extended position.
Figure 1D:
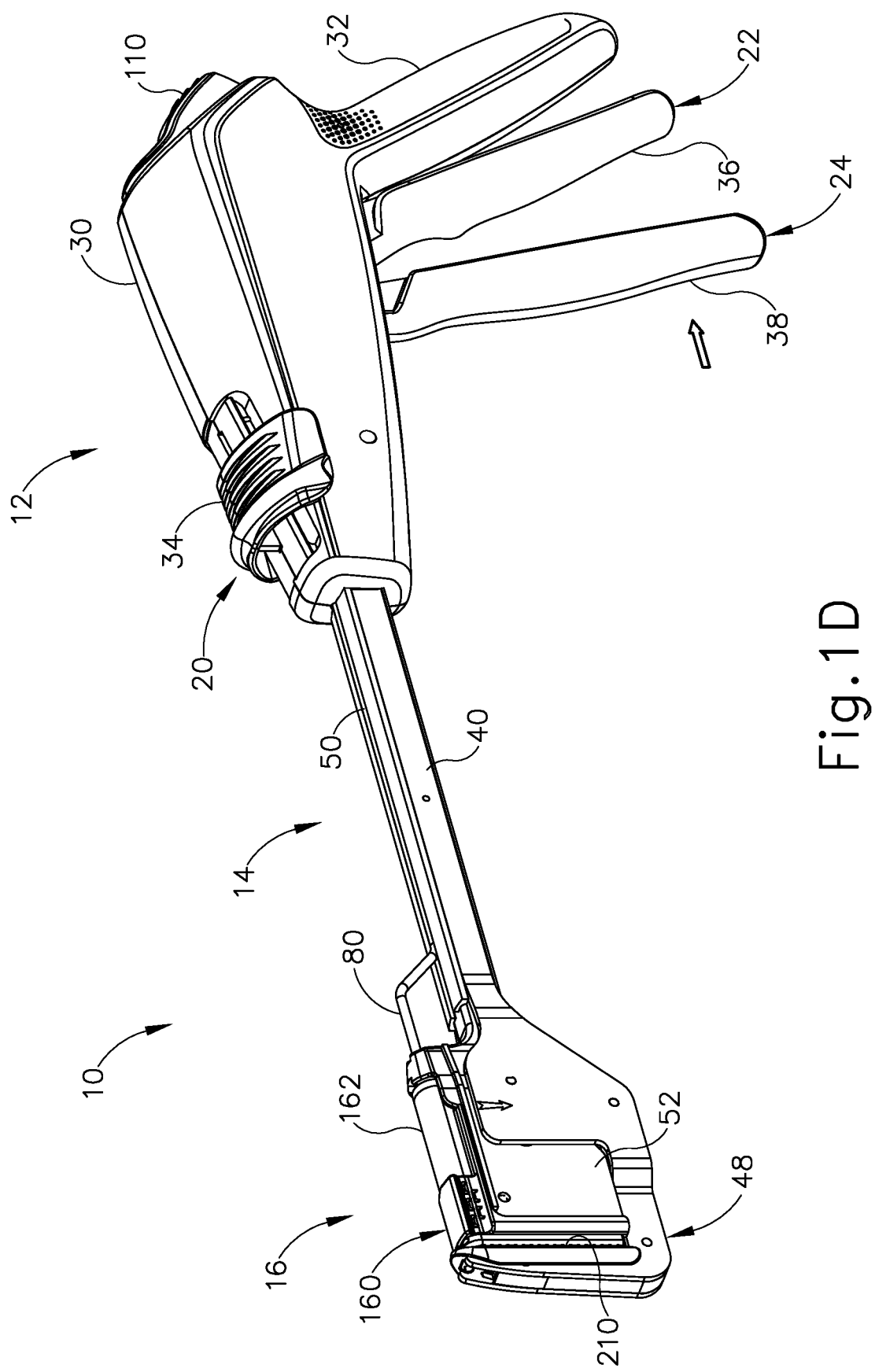
FIG. 1D depicts a perspective view of the surgical stapler of FIG. 1A, showing the end effector in a fired state via actuation of a firing system to effect stapling and cutting of tissue captured by the end effector, while the tissue retaining pin actuation system remains in the extended position.

As shown in FIG. 1A, handle assembly (12) includes a housing (30) that defines a pistol grip (32), a saddle shaped slide (34) slidably disposed on an upper portion of handle housing (30), a pivotable closure trigger (36), and a pivotable firing trigger (38). Closure trigger (36) and firing trigger (38) are operatively coupled with end effector (16) via shaft assembly (14) such that end effector (16) is configured to close and thereby clamp tissue in response to actuation of closure trigger (36), and subsequently staple and cut tissue (i.e., "fire") in response to actuation of firing trigger (38). FIG. 1A shows slide (34) and closure trigger (36) in unactuated configurations such that end effector (16) is configured to receive tissue laterally within a gap (G) (or "aperture") defined between a cartridge housing (162) and an anvil (210) of a replaceable staple cartridge unit (160) (or "reload") mounted within end effector (16). As shown in FIG. 1B, translating slide (34) distally toward end effector (16) extends a tissue retaining pin (176) of staple cartridge unit (160) distally for capturing the tissue between anvil (210) and cartridge housing (162). As shown in FIG. 1C, subsequently actuating closure trigger (36) toward pistol grip (32) drives cartridge housing (162) distally toward anvil (210), thereby clamping tissue therebetween. As shown in FIG. 1D, subsequently actuating firing trigger (38) toward pistol grip (32) drives staples distally into the clamped tissue and also cuts the tissue between formed staple lines with a knife member (194) (see FIG. 8), as described in greater detail below.

Figure 2:
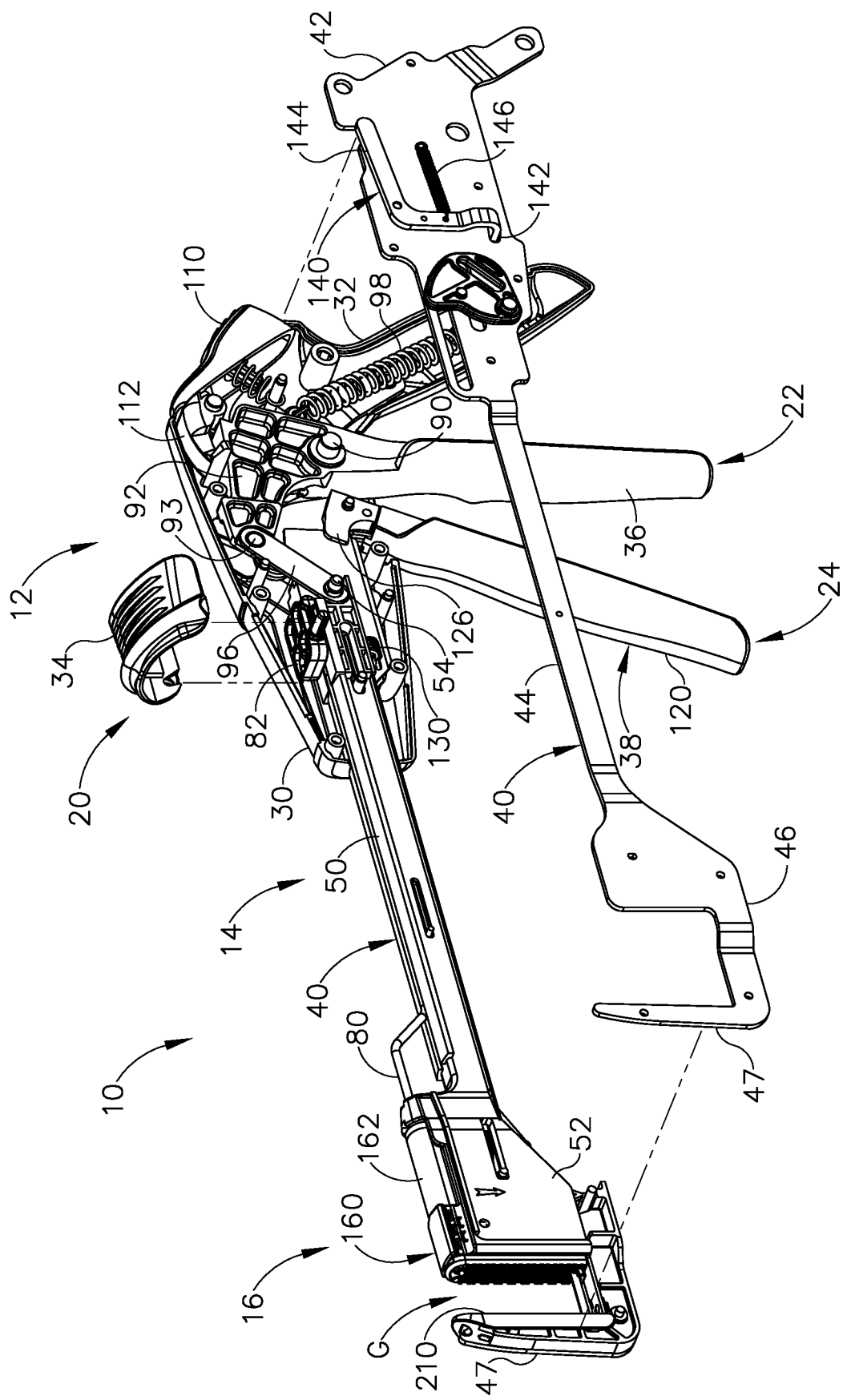
FIG. 2 depicts a partially disassembled perspective view of the surgical stapler of FIG. 1A.

As shown in FIG. 2, surgical stapler (10) includes a pair of longitudinally extending side plates (40) that cooperate to define a frame structure of stapler (10) that supports tissue retaining pin actuation system (20), closure system (22), and firing system (24). Each side plate (40) includes a proximal frame portion (42) housed within handle housing (30); a medial shaft portion (44) that defines a respective outer lateral side of shaft assembly (14); and a distal jaw portion (46) having an upwardly extending distal hook (47). Distal jaw portions (46) cooperate with the distal end of a closure bar (50), described below, to define a U-shaped distal support structure (48) of end effector (16) that removably receives staple cartridge unit (160). As used herein, the term "U-shaped" refers to the shape presented by end effector (16) in any of the side elevational views depicted herein.

As shown in FIG. 3, slidably disposed between and supported by side plates (40) are elongate actuatable components of actuation systems (20, 22, 24), which operatively couple handle assembly (12) with staple cartridge unit (160); including a closure bar (50), a staple bar (60), and a knife bar (70). Closure bar (50) includes a cartridge-receiving distal portion (52) configured to receive and support staple cartridge unit (160). Closure bar (50) and staple bar (60) are each configured as a double-sided structure having first and second lateral sides spaced apart from one another, and an inner channel extending longitudinally therebetween. This configuration enables an arrangement of shaft assembly (14) in which knife bar (70) is nested and slidably disposed within the longitudinal inner channel of staple bar (60), and in which staple bar (60) in turn is nested and slidably disposed within the longitudinal inner channel of closure bar (50). Moreover, staple bar (60) and knife bar (70) are longitudinally translatable independently of closure bar (50) through a range of longitudinal motion that enables independent closure and firing of end effector (16). As described in greater detail below, closure bar (50) is operable to actuate cartridge housing (162) longitudinally relative to anvil (210) for clamping tissue in response to actuation of closure trigger (36). Staple bar (60) is operable to actuate a staple driver member (186) (see FIG. 8) longitudinally relative to cartridge housing (162) for stapling the clamped tissue. Knife bar (70) is operable to actuate knife member (194) (see FIG. 8) longitudinally relative to cartridge housing (162) and staple driver member (186) for cutting the clamped tissue.

Tissue retaining pin actuation system (20) of surgical stapler (10) includes slide (34) of handle assembly (12), tissue retaining pin (176) of staple cartridge unit (160), an elongate pushrod (80) extending longitudinally along an upper side of shaft assembly (14), and a pushrod driver (82) slidably disposed within handle assembly (12). A distal end of pushrod (80) is configured to releasably couple with tissue retaining pin (176) upon insertion of staple cartridge unit (160) into distal support structure (48) of end effector (16). A proximal end of pushrod (80) is coupled with pushrod driver (82), which in turn is coupled with slide (34). Accordingly, longitudinal translation of slide (34) between proximal and distal positions drives longitudinal translation of tissue retaining pin (176) relative to cartridge housing (162) between retracted and extended positions. As shown in FIG. 1A, tissue retaining pin (176) is configured to assume a retracted position in which retaining pin (176) is housed within cartridge housing (162) when slide (34) is in a proximal position. As shown in FIG. 1B, tissue retaining pin (176) is configured to assume an extended position in which a distal end of retaining pin (176) engages anvil (210), thereby retaining tissue positioned within gap (G) of staple cartridge unit (160), when slide (34) is advanced to the distal position.

Closure system (22) of surgical stapler (10) includes closure trigger (36) of handle assembly (12) and closure bar (50). As shown in FIGS. 2 and 4A-4C, closure trigger (36) is pivotably coupled with handle housing (30) about a pair of laterally extending posts (90). An upper arm (92) of closure trigger (36) having a vertically slotted distal portion is operatively coupled with a proximal end of closure bar (50) by a pair of closure links (96). A proximal end of each closure link (96) is pivotably coupled with a laterally extending post (93) of closure trigger upper arm (92). A distal end of each closure link (96) is pivotably coupled with the proximal end of closure bar (50) about a laterally extending post (54) of closure bar (50).

Figure 4A:
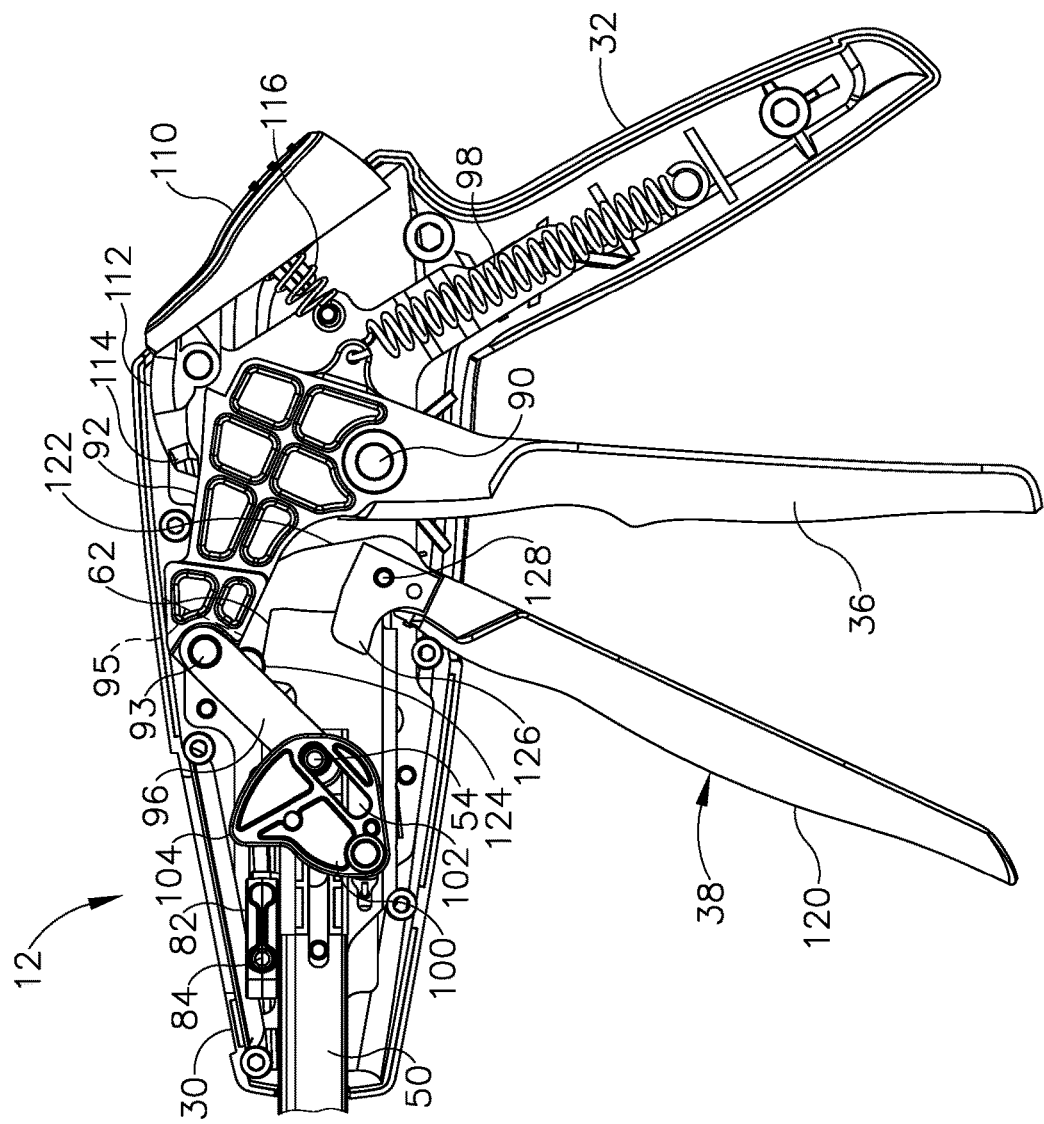
FIG. 4A depicts a side elevational view of the handle assembly of the surgical stapler of FIG. 1A, with various components omitted for clarity, showing the tissue retaining pin actuation system in an extended position to retain tissue while the closure system and the firing system are in unactuated states.
Figure 4B:
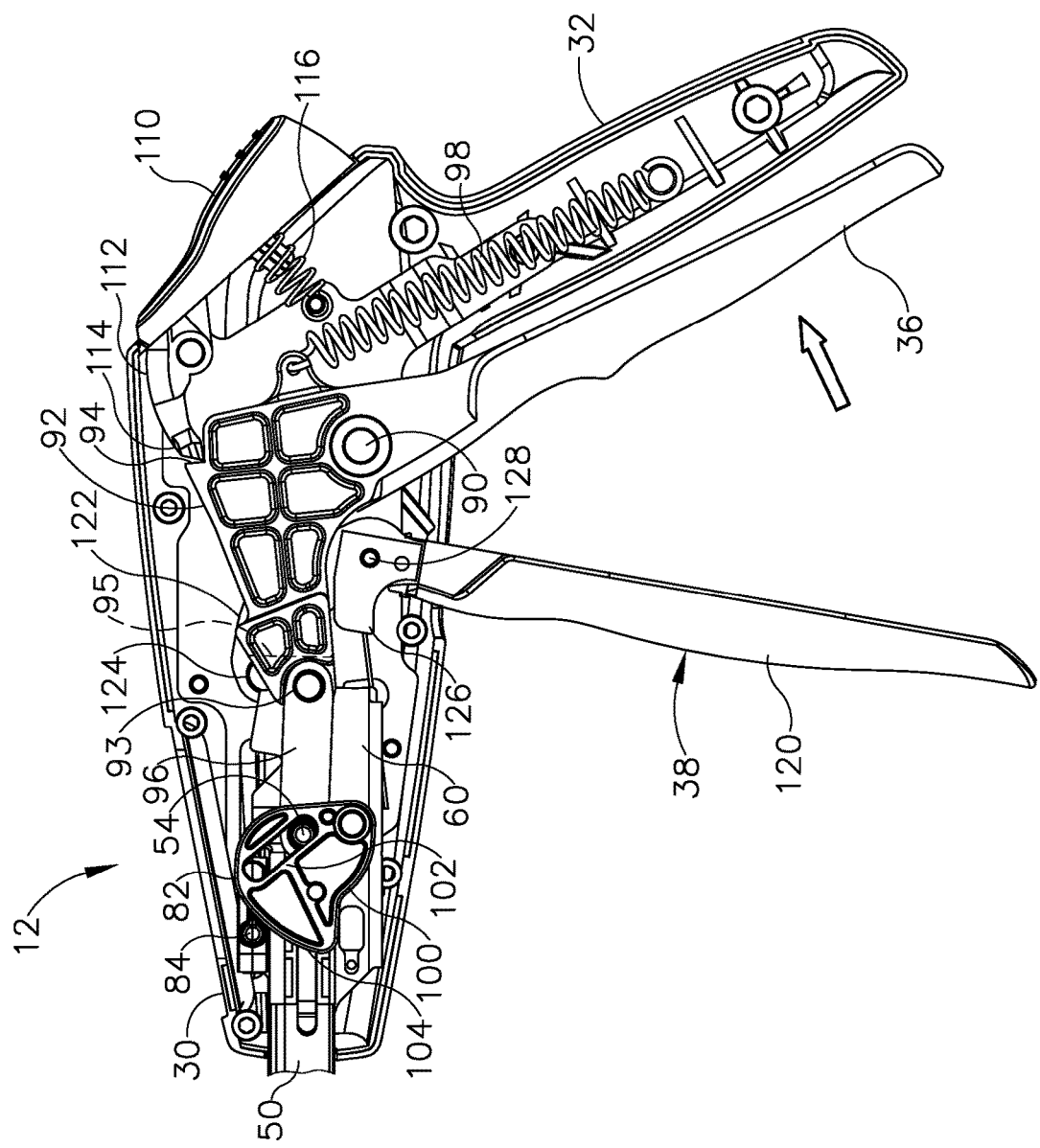
FIG. 4B depicts a side elevational view of the handle assembly of the surgical stapler of FIG. 1A, with various components omitted for clarity, showing the closure system actuated via a closure trigger to close the end effector and thereby clamp tissue.

As shown in FIGS. 4A-4B, pivoting of closure trigger (36) toward pistol grip (32) pivots advances closure trigger upper arm (92) distally and downwardly, thereby driving closure bar (50) distally via closure links (96). In turn, cartridge-receiving distal portion (52) of closure bar (50) drives cartridge housing (162) distally toward anvil (210). In this manner, end effector (16) is actuated from an open state (FIGS. 1A-1B) in which tissue is positionable within end effector (16), to a closed state (FIG. 1C) in which the tissue is clamped between cartridge housing (162) and anvil (210). A closure return spring (98) housed within pistol grip (32) of handle assembly (12) resiliently biases closure trigger (36) toward the unactuated state, and thus end effector (16) toward the open state.

In the present version, closure bar (50) is further configured to cooperate with tissue retaining pin actuation system (20) to automatically actuate retaining pin (176) distally to its extended position when an operator squeezes closure trigger (36). In that regard, as shown best in FIGS. 4A-4B, handle assembly (12) further includes a pair of camming yokes (100) rotatably disposed along the outer sides of closure links (96). Each camming yoke (100) includes an angled slot (102) that slidably receives a respective proximal post (54) of closure bar (50). As closure trigger (36) is actuated toward pistol grip (32), proximal posts (54) rotatably drive camming yokes (100) distally such that cam lobes (104) of yokes (100) engage corresponding side posts (84) of pushrod driver (82), thereby actuating pushrod (80) and thus tissue retaining pin (176) distally. Such automatic extension of tissue retaining pin (176) during closure of end effector (16) may be useful in the event that the operator does not manually actuate retaining pin (176) distally via slide (34) prior to actuating closure trigger (36).

Closure system (22) of the present example is further configured to releasably lock closure trigger (36) in the actuated position to provide effective clamping of tissue with end effector (16) without having to continuously squeeze closure trigger (36). As shown best in FIGS. 4A-4B, a release button (110) is pivotably disposed at a proximal end of handle assembly (12). A locking pawl (112) extends distally from an upper end of release button (110) and includes a pawl lug (114) that is resiliently biased into contact with an upper end of closure trigger upper arm (92), via a release button spring (116). Accordingly, pawl lug (114) is configured to slide along an upper surface of closure trigger upper arm (92) as closure trigger (36) is squeezed toward pistol grip (32). As shown in FIG. 4B, upon closure trigger (36) reaching a fully actuated position, pawl lug (114) drops into a proximal upper notch (94) of closure trigger upper arm (92), thereby locking closure trigger (36) in the fully actuated position. Should the operator wish to then reopen end effector (16), for example to reposition tissue within end effector (16) or otherwise release tissue once firing is complete, the operator may depress release button (110) to disengage pawl lug (114) from closure trigger (36). Via the resilient bias provided by closure return spring (98), closure trigger (36) then returns to the unactuated state and end effector (16) returns to the open state, shown in FIGS. 1A and 4A.

Firing system (24) of surgical stapler (10) includes firing trigger (38) of handle assembly (12), staple bar (60), knife bar (70), and staple driver member (186) and knife member (194) of staple cartridge unit (160). Features of knife bar (70) and staple driver member (186) are described in greater detail below in connection with FIG. 8. As shown in FIGS. 2 and 4A, firing trigger (38) of the present example is configured as an assembly having a lower shroud (120) that extends downwardly from handle housing (30) and is engageable by an operator; a pair of plates having arcuate upper arms (122) that extend upwardly and distally from lower shroud (120) and are positioned with handle housing (30); a rotatable cam pin (124) extending laterally between the free distal upper ends of arcuate upper arms (122); and a firing lockout projection (126) extending distally from the lower ends of arcuate upper arms (122) within handle housing (30). Cam pin (124) and other features of firing trigger (38) may be configured and operable in accordance with at least some of the teachings of U.S. patent application Ser. No. 16/395,359, entitled "Cartridge Based Lockout Mechanism for Right Angle Surgical Stapler," filed on Apr. 26, 2019, published as U.S. Pub. No. 2020/0337700 on Oct. 29, 2020, the disclosure of which is incorporated by reference herein.

Firing trigger (38) is pivotably coupled with handle housing (30) via a laterally extending pivot pin (128). Additionally, firing trigger (38) is positioned distal to closure trigger (36) such that arcuate upper arms (122) of firing trigger (38) are received into the slotted distal portion of closure trigger upper arm (92) as closure trigger (36) is actuated toward pistol grip (32). As shown in FIGS. 4A-4B, as the operator squeezes closure trigger (36) fully toward pistol grip (32), distally facing ledges (95) disposed within the distal slotted portion of closure trigger upper arm (92) engage cam pin (124) of firing trigger (38) and drive cam pin (124) distally by an initial amount. This causes the lower end of firing trigger (38) to pivot partially toward pistol grip (32) simultaneously with closure trigger (36), as shown in FIG. 4B.

Figure 4C:
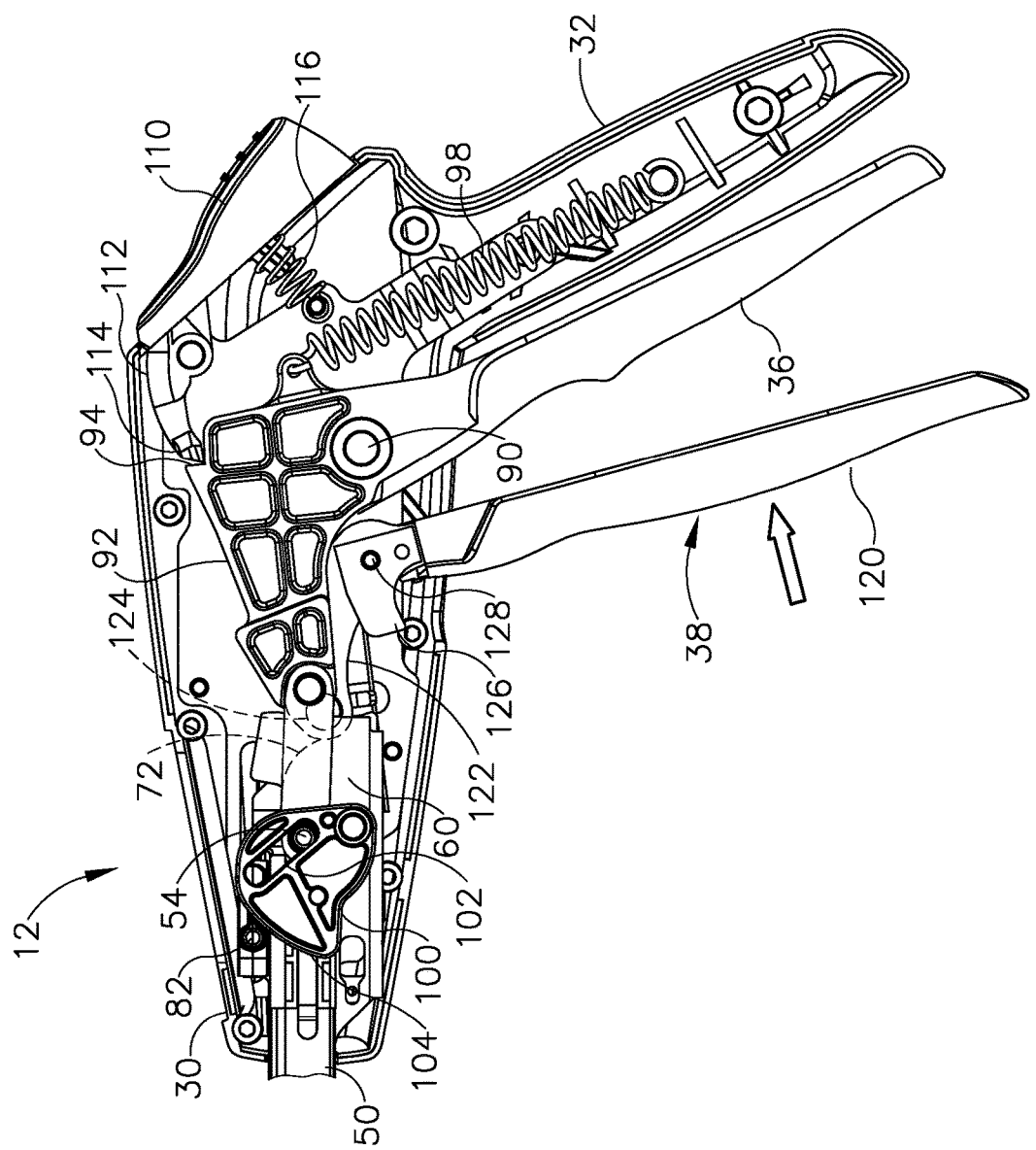
FIG. 4C depicts a side elevational view of the handle assembly of the surgical stapler of FIG. 1A, with various components omitted for clarity, showing the firing system actuated via a firing trigger to fire the end effector and thereby staple and cut tissue while the end effector remains in the closed state.
Figure 5:
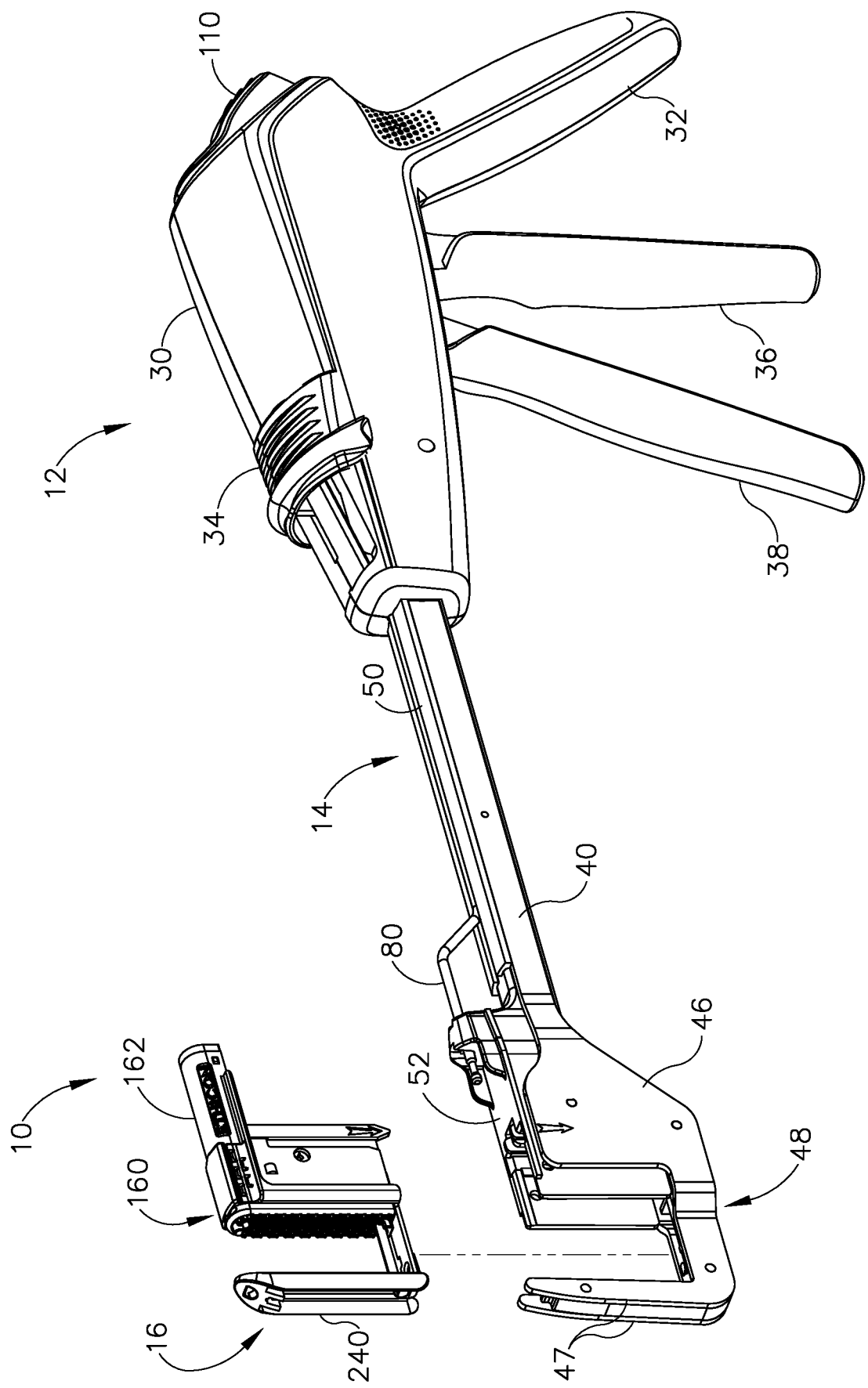
FIG. 5 depicts a perspective view of the surgical stapler of FIG. 1A, showing a staple cartridge unit of the end effector separated from a distal support structure of the end effector.

As shown in FIG. 4C, once end effector (16) has reached the fully closed state, further actuation of firing trigger (38) toward pistol grip (32) operates to "fire" end effector (16). In particular, outer portions of cam pin (124) engage proximal edges (62) of staple bar (60), thus driving staple bar (60) distally relative to closure bar (50). As described in greater detail below in connection with FIGS. 12A-12D, distal edges (64) of staple bar (60) engage a proximal end of staple driver member (186) within staple cartridge housing (162), thus driving staple driver member (186) distally through staple cartridge housing (162) to drive staples into tissue clamped by end effector (16). Actuation of firing trigger (38) toward its fully actuated state also causes a medial portion of cam pin (124), disposed between arcuate upper arms (122) of firing trigger (38), to engage a rounded proximal edge (72) of knife bar (70), thus driving knife bar (70) distally relative to closure bar (50). As described in greater detail below in connection with FIGS. 12A-12D, a distal edge (74) of knife bar (70) engages a proximal end of knife member (194) within staple cartridge housing (162), thus driving knife member (194) distally through staple driver member (186) to cut the tissue clamped by end effector (16).

Firing system (24) of the present example is suitably configured such that staple bar (60) and knife bar (70) translate distally together as firing trigger (38) is actuated through a primary range of motion toward pistol grip (32); and such that knife bar (70) continues to translate distally relative to staple bar (60) as firing trigger (38) is further actuated through a final range of motion toward pistol grip (32). Advantageously, such a configuration ensures that the tissue clamped by end effector (16) is fully stapled and that proper hemostasis is thus achieved along the intended tissue cut line before the tissue is cut by knife member (194).

As shown in FIG. 2, firing system (24) further includes a knife return spring (130) housed within handle assembly (12). Knife return spring (130) is anchored at its distal end to the distal end of knife bar (70), and at its proximal end to the distal end of closure bar (50). Accordingly, knife return spring (130) is operable to resiliently bias knife bar (70) proximally relative to closure bar (50) and staple bar (60) when firing trigger (38) is released. As shown in FIGS. 3 and 12A-12D, knife bar (70) includes a distal hook (76) that is captured by knife member (194) to thereby secure knife member (194) axially to knife bar (70). Accordingly, when the operator releases firing trigger (38) after completing a firing stroke, knife bar (70) and knife member (194) automatically retract proximally to safely house a distal cutting edge (200) of knife member (194) within staple cartridge housing (162).

As shown in FIG. 2, surgical stapler (10) of the present example further includes a proximal firing lockout mechanism in the form of a pivotable lever (140), which is operable to inhibit actuation of firing trigger (38) until end effector (16) has been fully closed by closure trigger (36). Firing lockout lever (140) is housed within handle assembly (12) and is pivotably mounted to an outer side of the proximal frame portion (42) of the left side plate (40). Firing lockout lever (140) is resiliently biased by a spring (146) toward a position in which a lower tab (142) of proximal lockout lever (140) blocks downward movement of firing lockout projection (126) of firing trigger (38), thus inhibiting actuation of firing trigger (38) when closure trigger (36) has not been fully actuated to close end effector (16). When closure trigger (36) reaches a fully actuated state, an upper arm (144) of firing lockout lever (140) is driven downwardly by pawl lug (114) of release button (110), thus rotating lower tab (142) away from firing lockout projection (126) and permitting actuation of firing trigger (38). Firing lockout lever (140) and other lockout features of surgical stapler (10) may be further configured and operable in accordance with at least some of the teachings of U.S. patent application Ser. No. 16/395,358, entitled "Clamping Based Lockout Mechanism for Right Angle Surgical Stapler," filed on Apr. 26, 2019, published as U.S. Pub. No. 2020/0337699 on Oct. 29, 2020, the disclosure of which is incorporated by reference herein.

Though not shown, shaft assembly (14) of surgical stapler (10) may include various additional components, such as an articulating joint, or may include a rearrangement of various components such that shaft assembly (14) may be modular relative to handle assembly (12).

B. End Effector of Surgical Stapler

End effector (16) of surgical stapler (10) includes distal support structure (48) defined by distal portions of side plates (40), cartridge-receiving distal portion (52) of closure bar (50), distal portions of staple bar (60) and knife bar (70), and replaceable staple cartridge unit (160). As shown best in FIGS. 5-8, staple cartridge unit (160) of the present version includes cartridge housing (162) and anvil (210) spaced apart from one another so as to define an axial gap (G) therebetween for receiving patient tissue to be stapled and cut. Cartridge housing (162) includes a distally facing deck (164) that is configured to clamp tissue against anvil (210) and extends transversely to a longitudinal axis of shaft assembly (14), along with anvil (210), thus providing end effector (16) with a "right angle" configuration.

Cartridge deck (164) includes an elongate linear knife slot (166) configured to slidably receive a knife (198) therethrough, and a plurality of staple openings (168) arranged in linear rows along either side of elongate linear knife slot (166) and configured to house a plurality of unformed staples (170) therein. Deck (164) of the present example further includes a plurality of stand-off features (172) interposed with staple openings (168) and configured to optimize grip and compression of patient tissue as the tissue is clamped between deck (164) and anvil (210). Deck (164) may be further configured in accordance with at least some of the teachings of U.S. patent application Ser. No. 16/234, 740, entitled "Surgical Stapler with Sloped Staple Deck for Varying Tissue Compression," filed Jan. 14, 2019, published as U.S. Pub. No. 2020/0205811 on Jul. 2, 2020, the disclosure of which is incorporated by reference herein.

An elongate upper body portion (174) of cartridge housing (162) slidably houses tissue retaining pin (176) and a couplet (180) secured to a proximal end of tissue retaining pin (176). Couplet (180) is configured to releasably couple tissue retaining pin (176) with a distal end of pushrod (80) of tissue retaining pin actuation system (20) when staple cartridge unit (160) is seated within distal support structure (48) of end effector (16). An end cap member (182) secured to a proximal end of upper body portion (174) is configured to constrain tissue retaining pin (176) and couplet (180) proximally within cartridge housing (162), while permitting tissue retaining pin (176) to translate between its proximal retracted position (see FIGS. 1A and 12A), and its distal extended position (see FIGS. 1B and 12B). Tissue retaining pin (176) includes a tapered distal tip (178) that is configured to pierce tissue as retaining pin (176) is extended toward anvil (210).

A lower body portion (184) of cartridge housing (162) slidably receives staple driver member (186) and knife member (194) therein. As shown best in FIG. 8, staple driver member (186) of the present version includes a base portion (188), a plurality of staple driver elements (190) projecting distally from base portion (188), and an interior channel (192) that extends axially through staple driver member (186) and is configured to slidably receive knife member (194). Each staple driver element (190) is configured to be slidably received within a respective staple opening (168) of cartridge housing (162) and drive a respective staple (170) from the opening (168) in response to actuation of closure trigger (36). While staple driver elements (190) of the present version are securely affixed to base portion (188), it will be appreciated that base portion (188) and staple driver elements (190) may be provided separately in other versions.

Knife member (194) includes a base portion (196) and a knife (198) secured to and extending distally from base portion (196) and having a distal cutting edge (200). Knife (198) is formed with a flat, plate-like shape that enables knife (198) to perform linear cuts on patient tissue. Knife member (194) is slidably received within interior channel (192) of staple driver member (186) such that knife (198) is configured to translate longitudinally through staple driver member (186) and elongate linear knife slot (166) of cartridge housing (162) for cutting tissue clamped by end effector (16) in response to full actuation of firing trigger (38).

Figure 8:
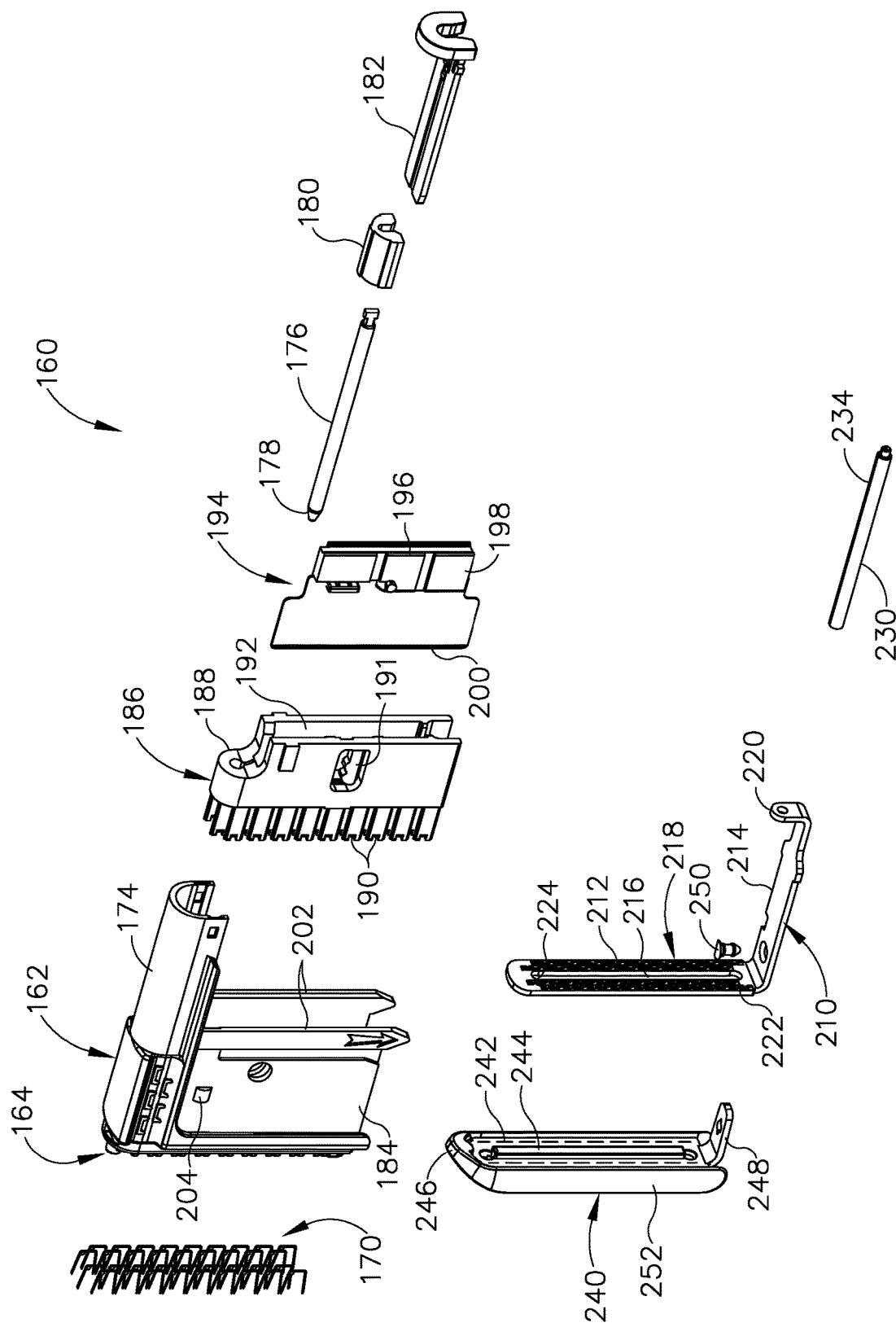
FIG. 8 depicts a disassembled perspective view of the staple cartridge unit of the surgical stapler of FIG. 1A.

As shown best in FIG. 8, anvil (210) of staple cartridge unit (160) includes a distal plate portion (212) and a coupling arm (214) extending proximally from a lower end of distal plate portion (212). Distal plate portion (212) is configured to cooperate with cartridge deck (164) to clamp tissue to be stapled and cut. Distal plate portion (212) includes an elongate linear slot (216) and a plurality of staple-forming pockets (218) arranged in linear rows along each side of slot (216). Pockets (218) are configured to receive and deform legs of staples (170) ejected from cartridge housing (162) for forming the staples (170) in tissue clamped between distal plate portion (212) and cartridge deck (164).

Figure 6:
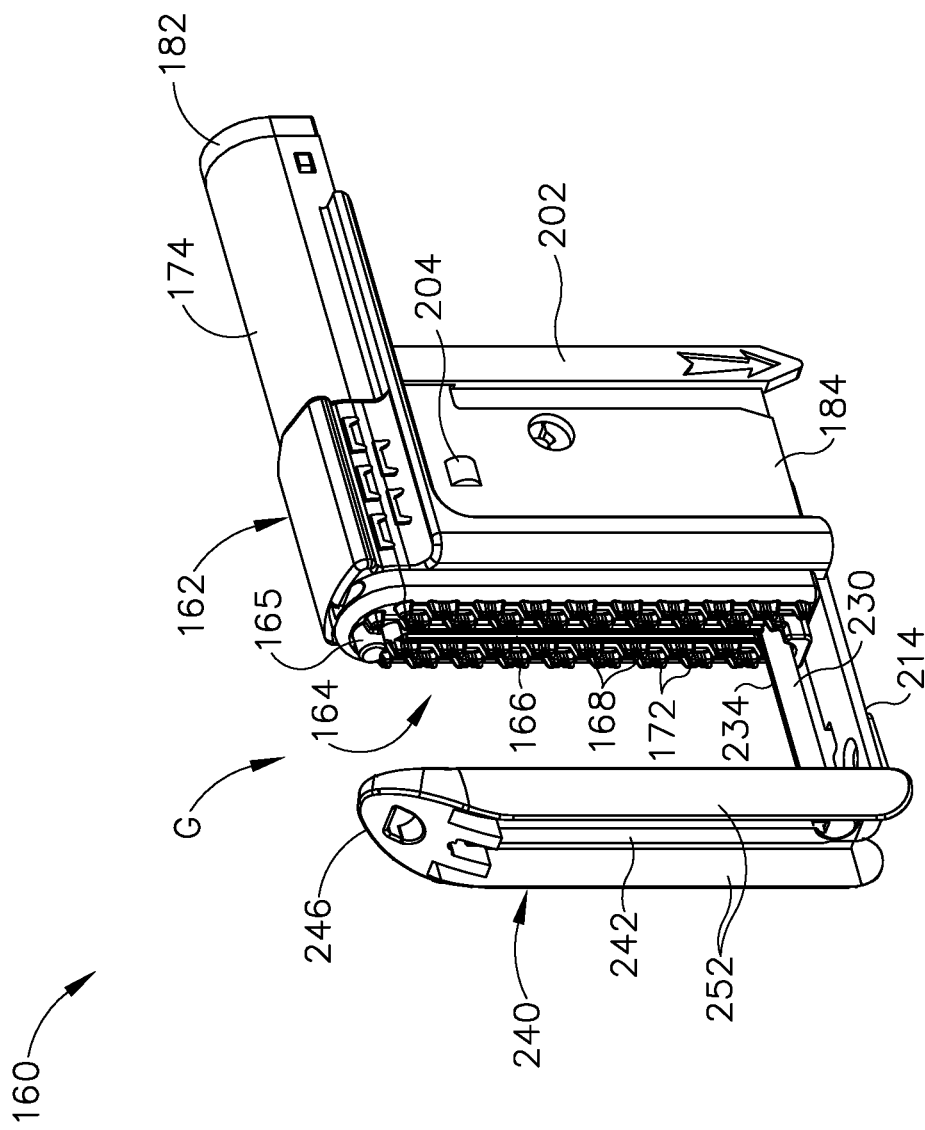
FIG. 6 depicts a distal left side perspective view of the staple cartridge unit of the surgical stapler of FIG. 1A.
Figure 7:
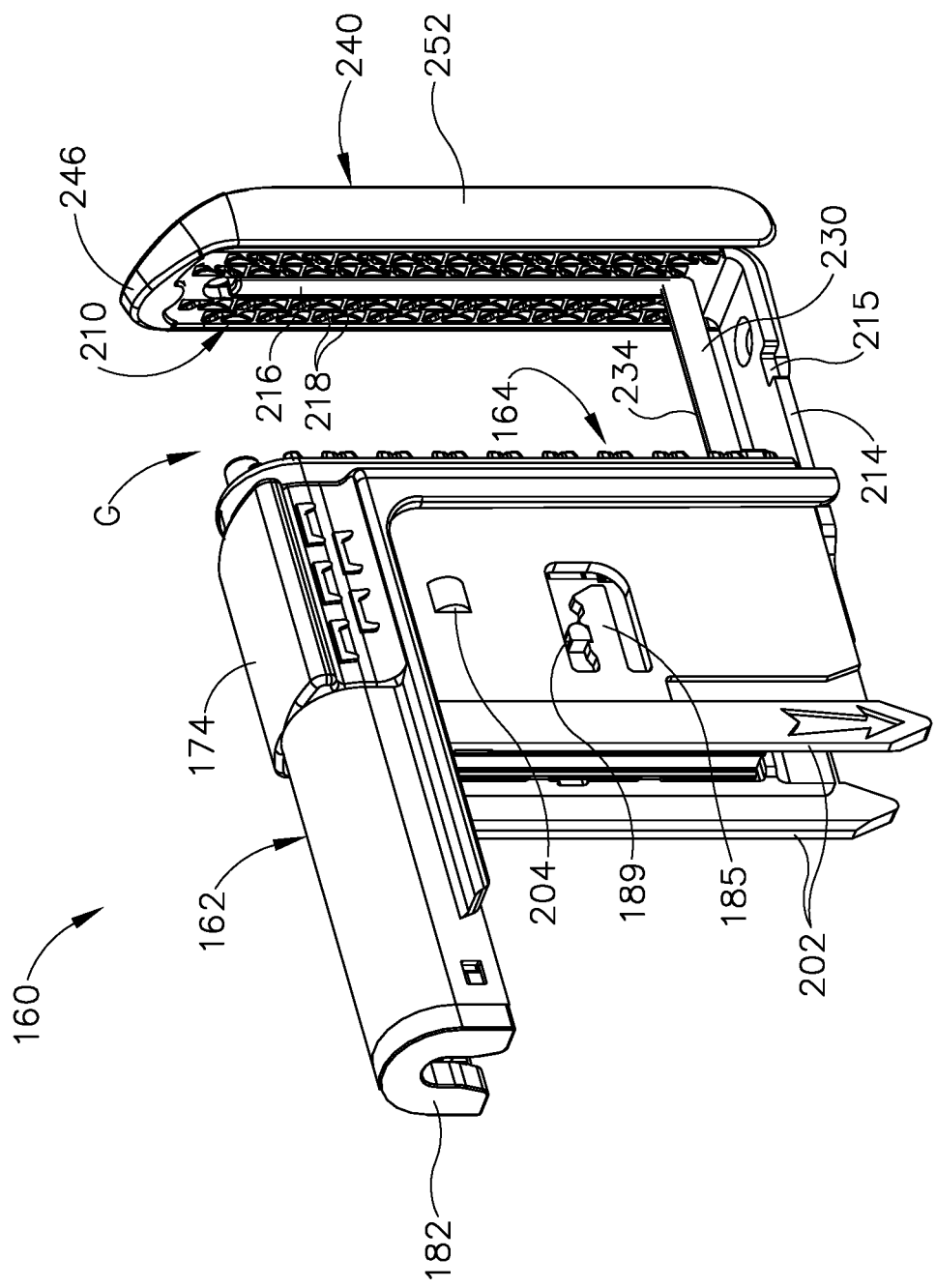
FIG. 7 depicts a proximal right side perspective view of the staple cartridge unit of the surgical stapler of FIG. 1A.
Figure 12A:
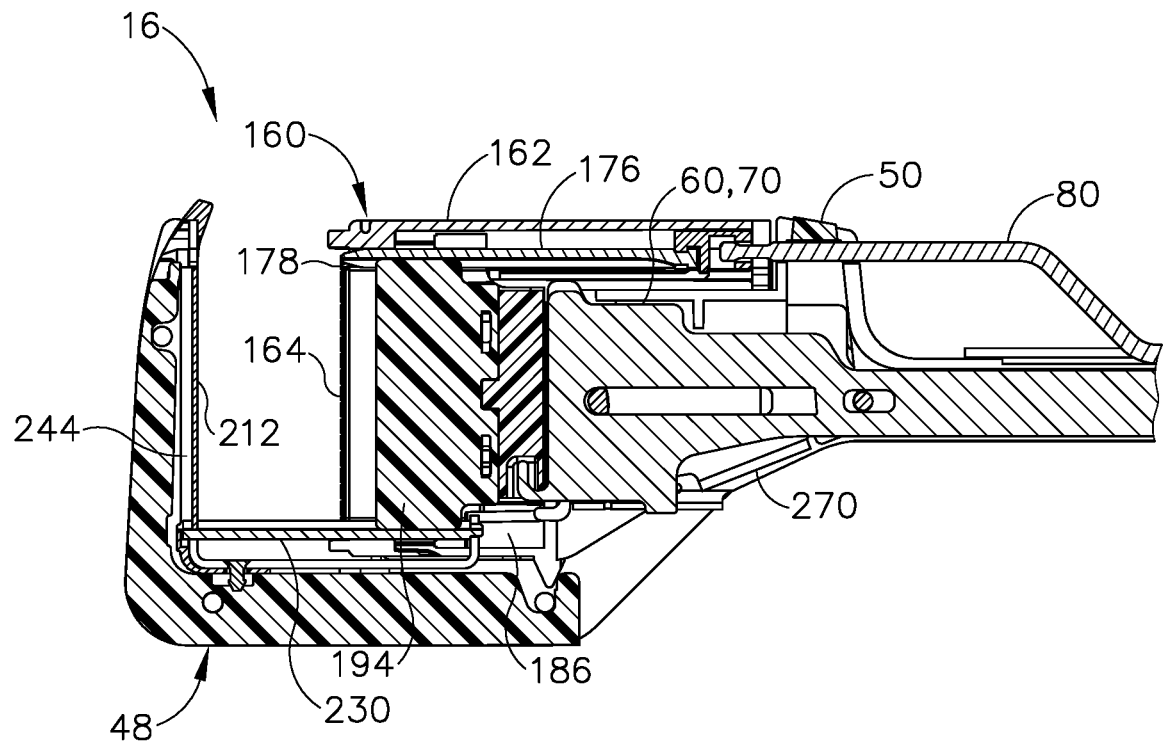
FIG. 12A depicts a side sectional view of the end effector of the surgical stapler of FIG. 1A, showing a tissue retaining pin in a retracted position while the end effector is in an open state.
Figure 12B:
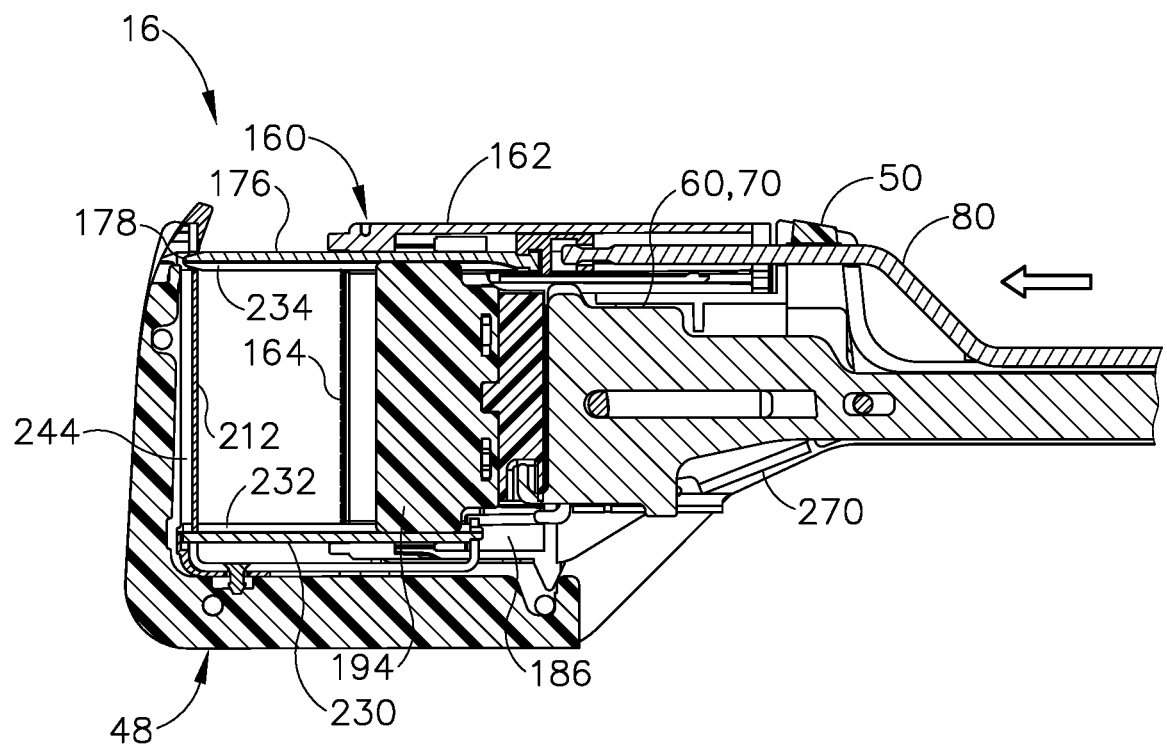
FIG. 12B depicts a side sectional view of the end effector of the surgical stapler of FIG. 1A, showing the tissue retaining pin in an extended position to retain tissue while the end effector remains in the open state.
Figure 12C:
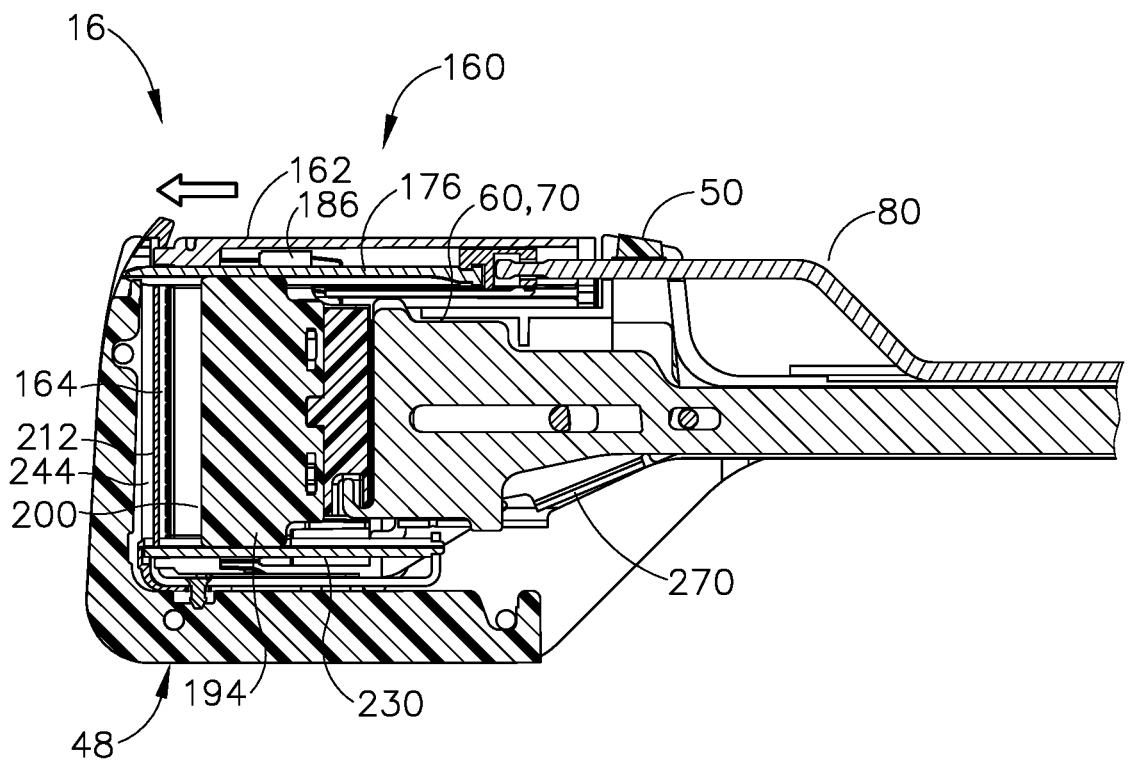
FIG. 12C depicts a side sectional view of the end effector of the surgical stapler of FIG. 1A, showing the end effector actuated to a closed state to clamp tissue while the tissue retaining pin remains in the extended position.

A guide pin (230) extends longitudinally between anvil plate portion (212) and cartridge housing (162) and is configured to guide longitudinal translation of cartridge housing (162) between the proximal open position (see FIGS. 1A and 12A) and the distal closed position (see FIGS. 1C and 12C). A proximal end of guide pin (230) is constrained by a proximal tab (220) of anvil coupling arm (214), shown in FIG. 8, and a distal end of guide pin (230) is constrained within a lower opening (222) formed in anvil plate portion (212). An upper opening (224) formed in anvil plate portion (212) is configured to receive and constrain tapered distal tip (178) of tissue retaining pin (176) in the extended position, such that tissue retaining pin (176) may cooperate with guide pin (230) to guide longitudinal translation of cartridge housing (162) relative to anvil (210). As seen in FIGS. 6-8, an inner side of guide pin (230) may include a longitudinal groove (232), which is configured to cooperate with a similar groove (234) (see FIGS. 12A-12D) to slidably guide knife (198) between retracted and extended positions relative to cartridge housing (162).

Staple cartridge unit (160) further includes a tissue cutting washer (240) fixed to anvil (210), and which is configured to cooperate with knife (198) to cut tissue clamped by end effector (16). As shown best in FIGS. 8 and 10-11, tissue cutting washer (240) includes an elongate, plate-like body (242) that extends along the distal side of anvil plate portion (212). Washer body (242) includes an elongate cutting element (244) that protrudes proximally through elongate slot (216) of anvil plate portion (212). Cutting element (244) functions as a cutting board by providing knife cutting edge (200) with a flat surface against which cutting edge (200) cuts tissue. At least cutting element (244) of tissue cutting washer (240) may comprise a polymeric material, such as high-density polyethylene (HDPE). In that regard, knife (198) may cut axially into cutting element (244), along its longitudinal centerline, when cutting tissue. While cutting element (244) of the present version provides a generally planar cutting surface, it will be appreciated that cutting element (244) may be alternatively configured in other versions.

Tissue cutting washer (240) further includes a rounded tip (246) at an upper end of washer body (242), and a coupling arm (248) extending proximally from a lower end of washer body (242). Washer tip (246) captures and thereby constrains an upper end of anvil plate portion (212), and its rounded configuration promotes atraumatic interaction with patient tissue. A press-fit pin (250) is configured to be inserted through openings formed in proximal coupling arms (214, 248) of anvil (210) and tissue cutting washer (240), thereby securely coupling anvil (210) and cutting washer (240) together.

Figure 10:
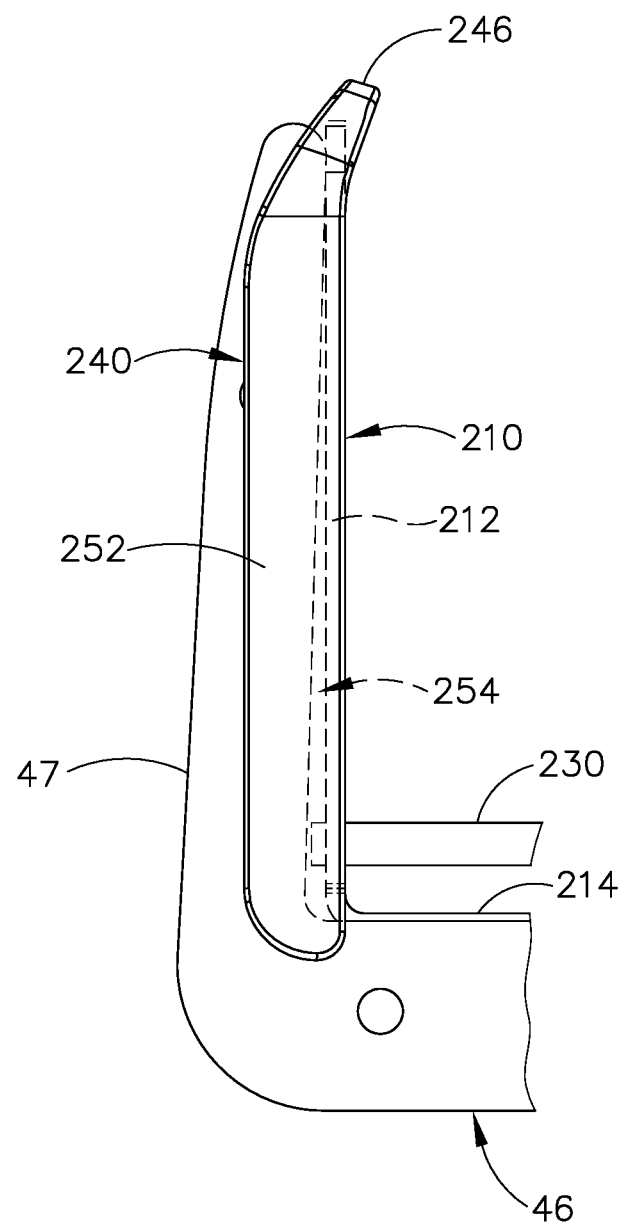
FIG. 10 depicts a side elevational view of a distal portion of the end effector of the surgical stapler of FIG. 1A following insertion of the staple cartridge unit into the distal support structure.
Figure 11:
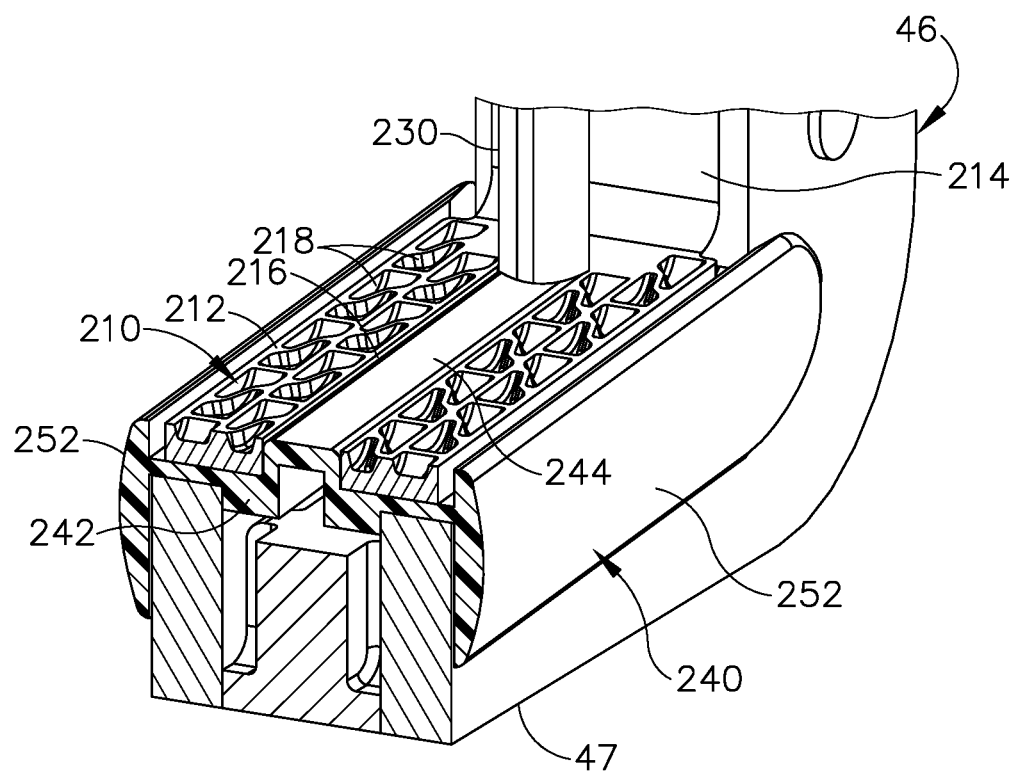
FIG. 11 depicts a sectional view of the distal portion of the end effector of the surgical stapler of FIG. 1A, showing interaction of a tissue cutting washer of the staple cartridge unit with the distal support structure.

Tissue cutting washer (240) further includes a pair of side flanges (252) that extend along a full length of anvil plate portion (212). As shown in FIGS. 10 and 11, each side flange (252) extends proximally to cover a respective side edge of anvil plate portion (212), and distally to cover at least a portion of distal hook (47) of the respective side plate (40) defining distal support structure (48). Accordingly, and advantageously, side flanges (252) function to cover an axial gap (254) that may form between anvil plate portion (212) and distal hooks (47), thereby preventing tissue from entering into and getting pinched within axial gap (254) in a manner that might otherwise result in undesirable trauma to the tissue. As shown in FIG. 11, the outer surfaces of side flanges (252) may be rounded to further enhance the atraumatic characteristics of the outer periphery of tissue cutting washer (240). Tissue cutting washer (240) may be further configured and operable in accordance with any of the teachings of U.S. patent application Ser. No. 16/395,357, entitled "Tissue Cutting Washer for Right Angle Surgical Stapler," filed on Apr. 26, 2019, published as U.S. Pub. No. 2020/0337698 on Oct. 29, 2020, the disclosure of which is incorporated by reference herein.

Figure 9B:
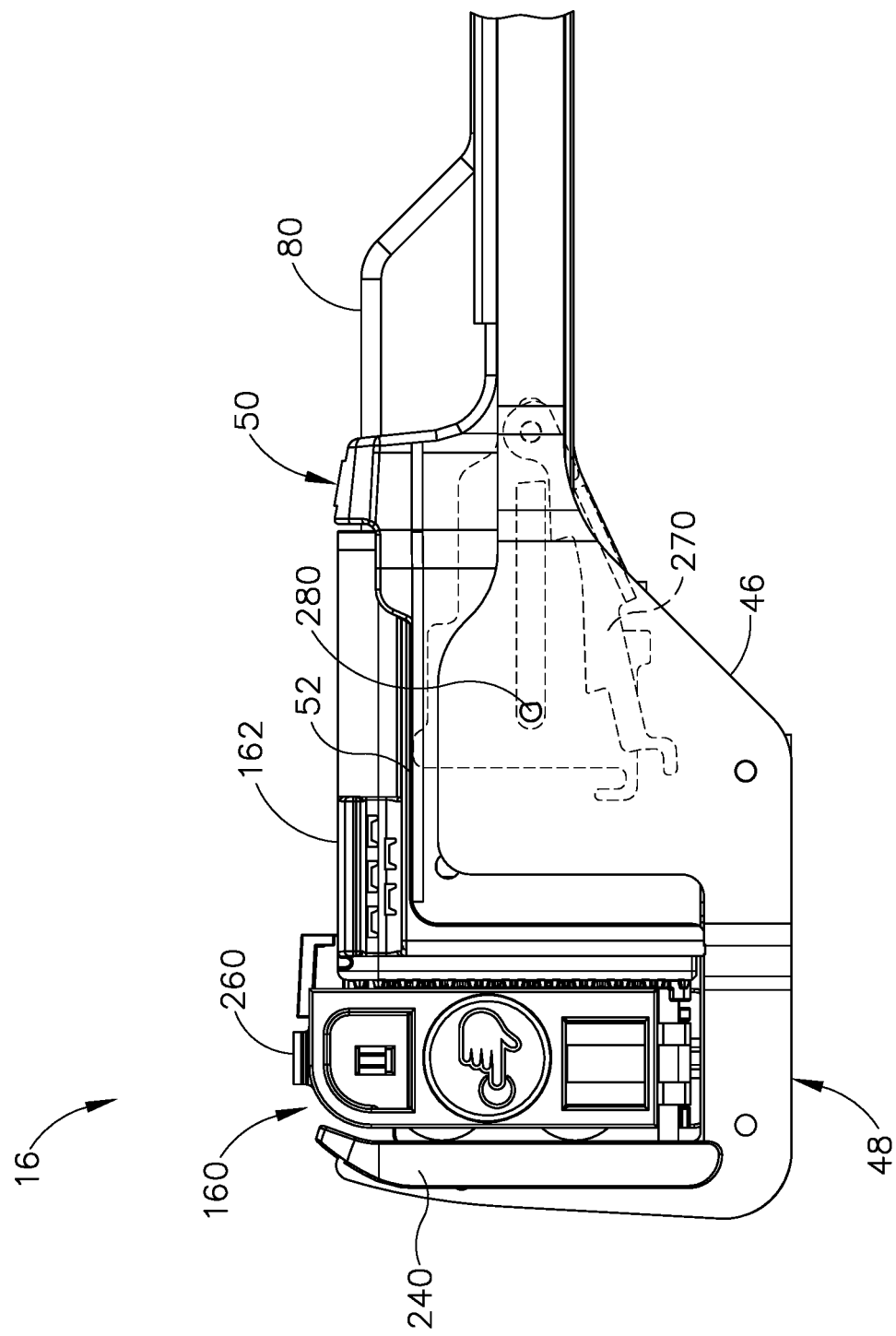
FIG. 9B depicts a side elevational view of the end effector of the surgical stapler of FIG. 1A, showing the lockout member in a bypass position when an unspent staple cartridge unit is seated within the distal support structure.

C. Exemplary Loading of Staple Cartridge Unit into Distal Support Structure of End Effector FIGS. 9A and 9B show loading of staple cartridge unit (160) in its unused (or "unspent") state into distal support structure (48) of end effector (16). As shown in FIG. 9A, and as described briefly above, distal support structure (48) is configured with a U-shaped side profile having a distal side defined by distal hooks (47), a proximal side defined by a proximal portion of distal jaw portion (46) and a distal end of cartridge-receiving distal portion (52) of closure bar (50), and an upwardly opening axial gap disposed therebetween.

Staple cartridge unit (160) is shown in FIGS. 9A-9B provided with a staple retainer (260) that is removably positioned between deck (164) and anvil plate portion (212) to retain staples (170) within staple openings (168), and to ensure proper axial spacing between deck (164) and anvil plate portion (212) as staple cartridge unit (160) is inserted into distal support structure (48). Upon removal of staple retainer (260), staple cartridge unit (160) presents a U-shaped side profile similar to that of distal support structure (48), with a distal side defined by anvil plate portion (212) and tissue cutting washer (240), a proximal side defined by cartridge deck (164), and upwardly opening axial gap (G) disposed therebetween. Exemplary features of staple retainer (260) are described in greater detail below in connection with FIGS. 13-18.

As shown in FIG. 9A, the user first aligns proximal side rails (202) formed on lower body portion (184) of cartridge housing (162) with inner channels (56) formed in cartridge-receiving distal portion (52) of closure bar (50) (see FIG. 3). As shown in FIG. 9B, the user then presses staple cartridge unit (160) downwardly into distal support structure (48) of end effector (16) such that proximal side rails (202) of cartridge housing (162) slide downwardly into inner channels (56) of closure bar (50), and such that distal hooks (47) of side plates (40) slide into grooves formed in the distal side of tissue cutting washer body (242) (see FIG. 11). As staple cartridge unit (160) fully seats within distal support structure (48), detent protrusions (204) formed on lower body portion (184) of cartridge housing (162) are receiving within respective openings (58) formed in cartridge-receiving distal portion (52) of closure bar (50), thereby removably securing staple cartridge unit (160) within distal support structure (48). Engagement of cartridge detent protrusions (204) with openings (58) may provide the user with tactile and/or audible feedback to confirm that staple cartridge unit (160) has been fully seated within distal support structure (48).

As shown in FIG. 9A, a distal lockout lever (270) is pivotably coupled to a distal end of staple bar (60). Distal lockout lever (270) extends distally toward distal edges (64) of staple bar (60) and knife bar (70) and is configured to releasably engage a fixed distal pin (280) that extends laterally through distal portions of side plates (40), closure bar (50), staple bar (60), and knife bar (70). Distal lockout lever (270) is resiliently biased toward a raised position shown in FIG. 9A and is pivotable toward a lowered position shown in FIG. 9B in response to engagement by a proximal end of staple driver member (186) upon insertion of an unspent staple cartridge unit (160) into distal support structure (48). In the raised position, distal lockout lever (270) lockingly engages fixed distal pin (280) and thereby inhibits distal actuation of staple bar (60) and knife bar (70), and thus firing of staple cartridge unit (160). In the lowered position, distal lockout lever (270) disengages fixed distal pin (280) and thus permits distal actuation of staple bar (60) and knife bar (70) for firing of staple cartridge unit (160). Distal lockout lever (270) and other lockout features of surgical stapler (10) may be further configured and operable in accordance with any of the teachings of U.S. patent application Ser. No. 16/395,359, entitled "Cartridge Based Lockout Mechanism for Right Angle Surgical Stapler," filed on Apr. 26, 2019, published as 2020/0337700 on Oct. 29, 2020, the disclosure of which is incorporated by reference herein.

D. Exemplary Actuation of Surgical Stapler

Having described various structural features of surgical stapler (10) above, including staple cartridge unit (160), exemplary actuation of surgical stapler (10) during a surgical procedure will now be described below. After loading an unspent staple cartridge unit (160) into distal support structure (48) in the manner described above, end effector (16) is then suitably manipulated within a body cavity of a patient to position patient tissue within staple cartridge gap (G), between anvil plate portion (212) and cartridge deck (164). As shown in FIGS. 12A and 12B, pushrod (80) is then actuated distally via slide (34) to drive pushrod (80) distally, thereby extending tissue retaining pin (176) from cartridge housing (162) so that its distal tip (178) pierces through any tissue overlying the upper end of cartridge deck (164) and seats within the upper end of anvil plate portion (212). In this manner, the patient tissue is securely retained within cartridge gap (G) before closure.

As shown in FIG. 12C, closure bar (50) is then actuated distally via closure trigger (36), thereby driving cartridge housing (162) distally along guide pin (230) and tissue retaining pin (176) to clamp tissue between cartridge deck (164) and anvil plate portion (212). As shown in the present example, staple bar (60) and knife bar (70) actuate distally with closure bar (50) and cartridge housing (162) so that staple driver member (186) and knife member (194) are suitably positioned for firing upon full closure of end effector (16). As described above, end effector (16) is releasably maintained in the fully closed state by locking pawl (112) of release button (110) of handle assembly (12).

Figure 12D:
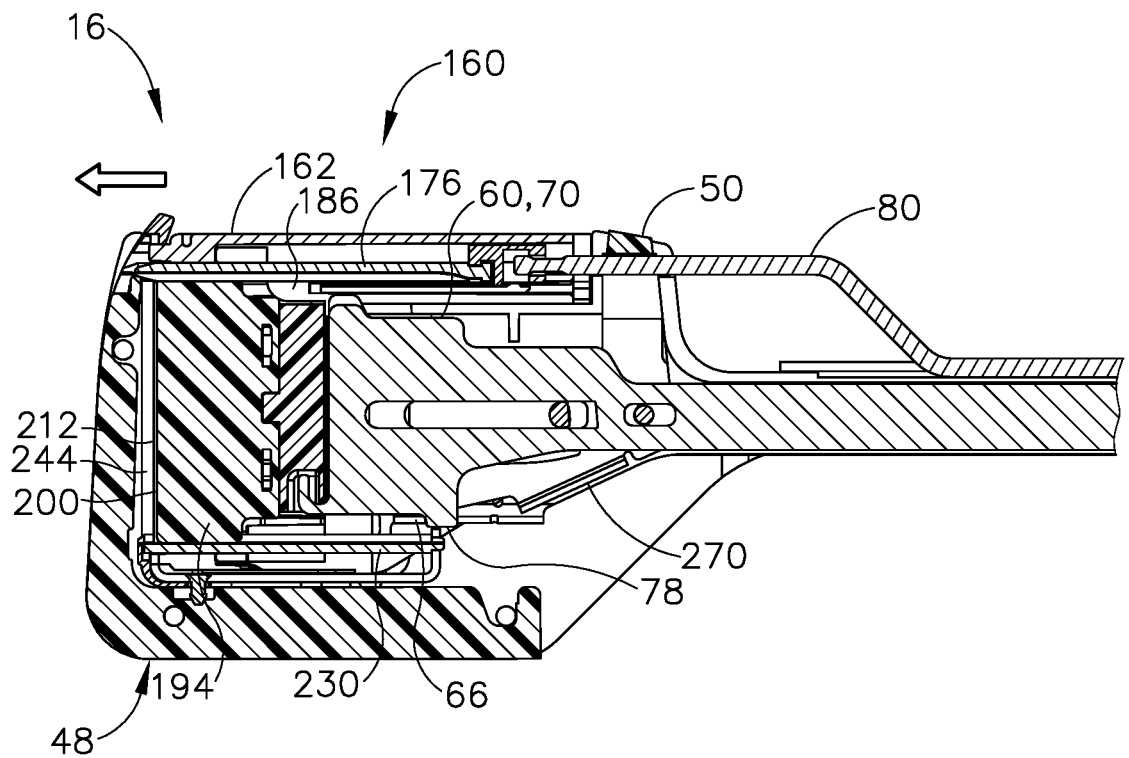
FIG. 12D depicts a side sectional view of the end effector of the surgical stapler of FIG. 1A, showing the end effector further actuated to a fired state to staple and cut tissue while remaining in the closed state.

As shown in FIG. 12D, staple bar (60) and knife bar (70) are then actuated distally via firing trigger (38), thereby driving staple driver member (186) and knife bar (70) distally through cartridge housing (162). Staple driver elements (190) of staple driver member (186) advance distally through staple openings (168), thereby driving staples (170) housed therein distally through the clamped tissue and into staple-forming pockets (218) of anvil plate portion (212), such that the staples (170) are formed in the tissue. Knife member (194) drives knife (198) distally through elongate knife slot (166) of cartridge deck (164), through the clamped tissue, and against cutting element (244) of tissue cutting washer (240), thereby severing the clamped tissue along a linear cut line between the innermost rows of formed staples (170). Upon cutting fully through the clamped tissue, knife cutting edge (200) may penetrate distally into cutting element (244) of tissue cutting washer (240). Optionally, in response to such penetration, tissue cutting washer body (242) may fracture along knife cutting edge (200), thereby providing an audible indication (e.g., via a "snapping" sound) to the surgeon that the firing stroke is complete and that the clamped tissue has been fully stapled and severed.

As described above, and as shown in FIG. 12D, staple driver member (186) and knife member (194) may translate distally together through staple cartridge housing (162) as firing trigger (38) is actuated through a primary range of motion that results in stapling of the tissue. As shown in FIG. 12D, knife member (194) may then continue translating distally relative to a stationary staple driver member (186) as firing trigger (38) is further actuated through a final range of motion that results in cutting of the stapled tissue with knife (198). In this manner, the tissue clamped by end effector (16) is fully stapled before being severed.

As shown best in FIG. 7, a first lateral side of lower body portion (184) of cartridge housing (162) includes a detent arm (185) having a plurality of axially spaced recesses. Additionally, a first lateral side of base portion (188) of staple driver member (186) includes a laterally extending detent post (189), which is configured to detent axially along detent arm (206) as staple driver member (186) is driven distally through cartridge housing (162) when stapling clamped tissue. As shown best in FIG. 8, a second lateral side of base portion (188) of staple driver member (186) includes a detent arm (191) having a plurality of axially spaced recesses. Additionally, a second lateral side of base portion (196) of knife member (194) includes a laterally extending detent post (197), which is configured to detent axially along detent arm (191) as knife member (194) is driven distally through staple driver member (186) when cutting clamped tissue. Such detent features may provide the surgeon with tactile feedback when staple driver member (186) has been fully extended to staple the tissue, and subsequently when knife member (194) has been fully extended to cut the stapled tissue.

Once surgical stapler (10) has been fully fired, the surgeon releases firing trigger (38), which enables knife bar (70) and knife member (194) to automatically retract proximally relative to closure bar (50) via the resilient bias of knife return spring (130), described above. In the present version, knife bar (70) is operatively coupled with staple bar (60) such that proximal retraction of knife bar (70) relative to closure bar (50) also drives proximal retraction of staple bar (60) relative to closure bar (50); for example, via engagement of a lower tab (78) formed on a distal portion of knife bar (70) with a lower slot (66) formed in the underside of a distal portion of staple bar (60). Meanwhile, stapling detent features (185, 189) described above operate to maintain staple driver member (186) in its fully extended position within cartridge housing (162), such that distal lockout lever (270) disengages staple driver member (186). This allows distal lockout lever (270) to return to a raised lockout position and block re-actuation of firing trigger (38) now that staple cartridge unit (160) is spent. In this manner, distal lockout lever (270) prevents a surgeon from inadvertently re-firing spent staple cartridge unit (160) into tissue in a manner that would sever the tissue with knife (198) without applying staples.

Following release of firing trigger (38), the surgeon then depresses release button (110) on handle assembly (12) to permit closure trigger (36) and closure bar (50) to return to their unactuated states via the resilient bias of closure return spring (98), described above. Such proximal retraction of closure bar (50) draws cartridge housing (162) proximally away from anvil (210) so that the stapled and cut tissue may be released from end effector (16). Proximal retraction of closure bar (50) also draws staple bar (60) and knife bar (70) further proximally to their proximal home positions so that spent staple cartridge unit (160) may be removed from distal support structure (48) and replaced with a new staple cartridge unit (160).

E. Exemplary Staple Retainer Having Resilient Contact Member

In various instances, it may be desirable to ensure that staples (170) are securely retained within staple openings (168) of cartridge deck (164) before staple cartridge unit (160) is seated within end effector (16), and before the operator is ready to deploy end effector (16) within a patient to staple and cut tissue. As described above, cartridge housing (162) is slidable relative to anvil (210) and tissue cutting washer (240) along pins (176, 230) between an open state in which an axial gap (G) (or "aperture") is defined therebetween for receiving tissue (see FIG. 1A), and a closed state for clamping the tissue. Accordingly, to facilitate proper loading of staple cartridge unit (160) into distal support structure (48) of surgical stapler (10), it may also be desirable to maintain this aperture along the full lengths of anvil plate portion (212) and cartridge deck (164), such that these components remain generally parallel to one another during loading.

As briefly described above in connection with FIGS. 9A-9B, staple retainer (260) is configured to be removably positioned between deck (164) and anvil plate portion (212) of staple cartridge unit (160), and may be removed by the operator when the operator is ready to deploy end effector (16) during a surgical procedure. Staple retainer (260) is operable to securely retain staples (170) within staple openings (168), and to ensure proper axial spacing between deck (164) and anvil plate portion (212) as staple cartridge unit (160) is loaded into distal support structure (48). Exemplary features of staple retainer (260) are described below in connection with FIGS. 13-20D. Advantageously, such features enable staple retainer (260) to be used as a universal part in connection with various staple cartridge units configured for stapling tissues of different thicknesses.

Figure 13:
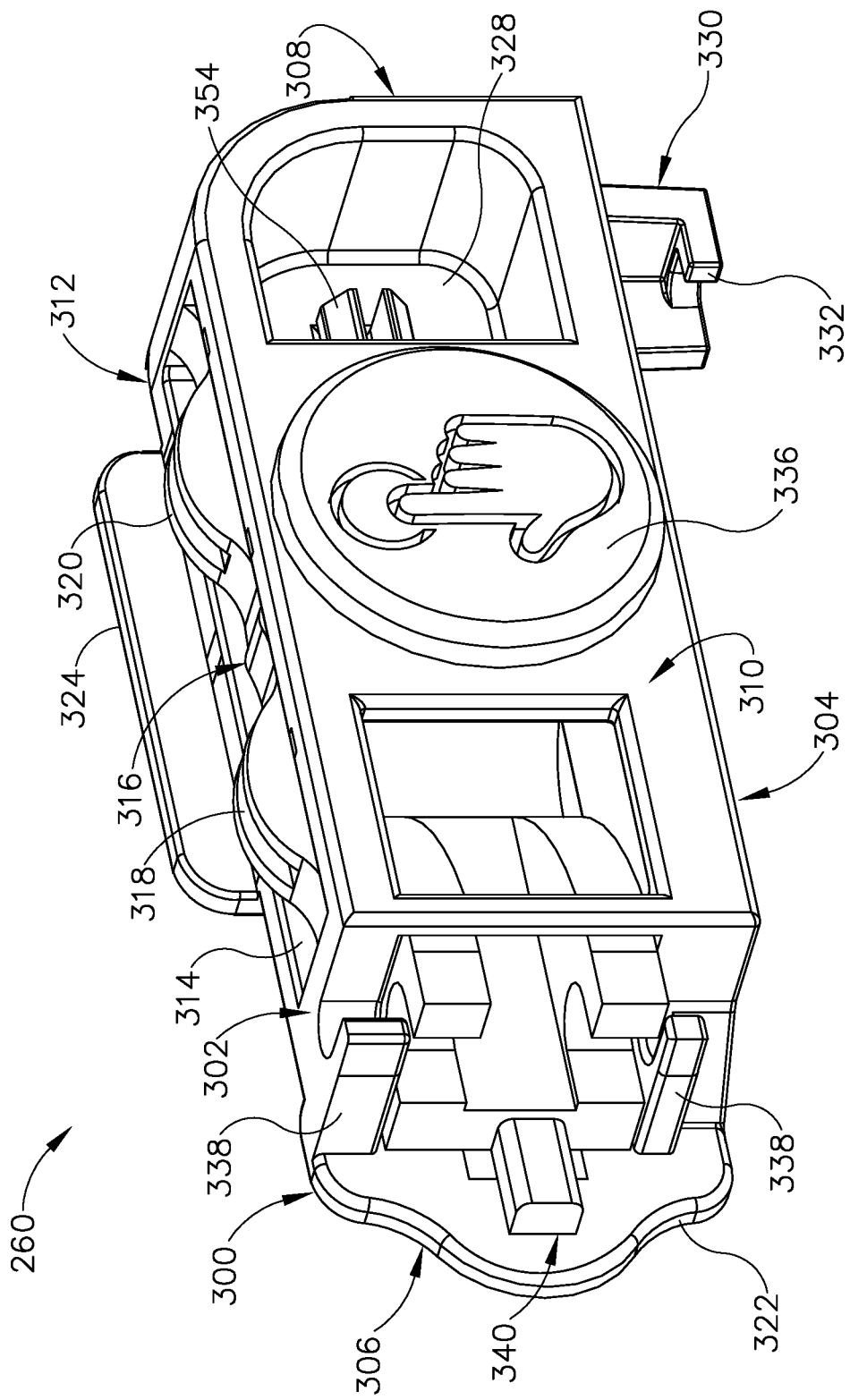
FIG. 13 depicts a front perspective view of an exemplary staple retainer configured for use with the staple cartridge unit of the surgical stapler of FIG. 1A.
Figure 14:
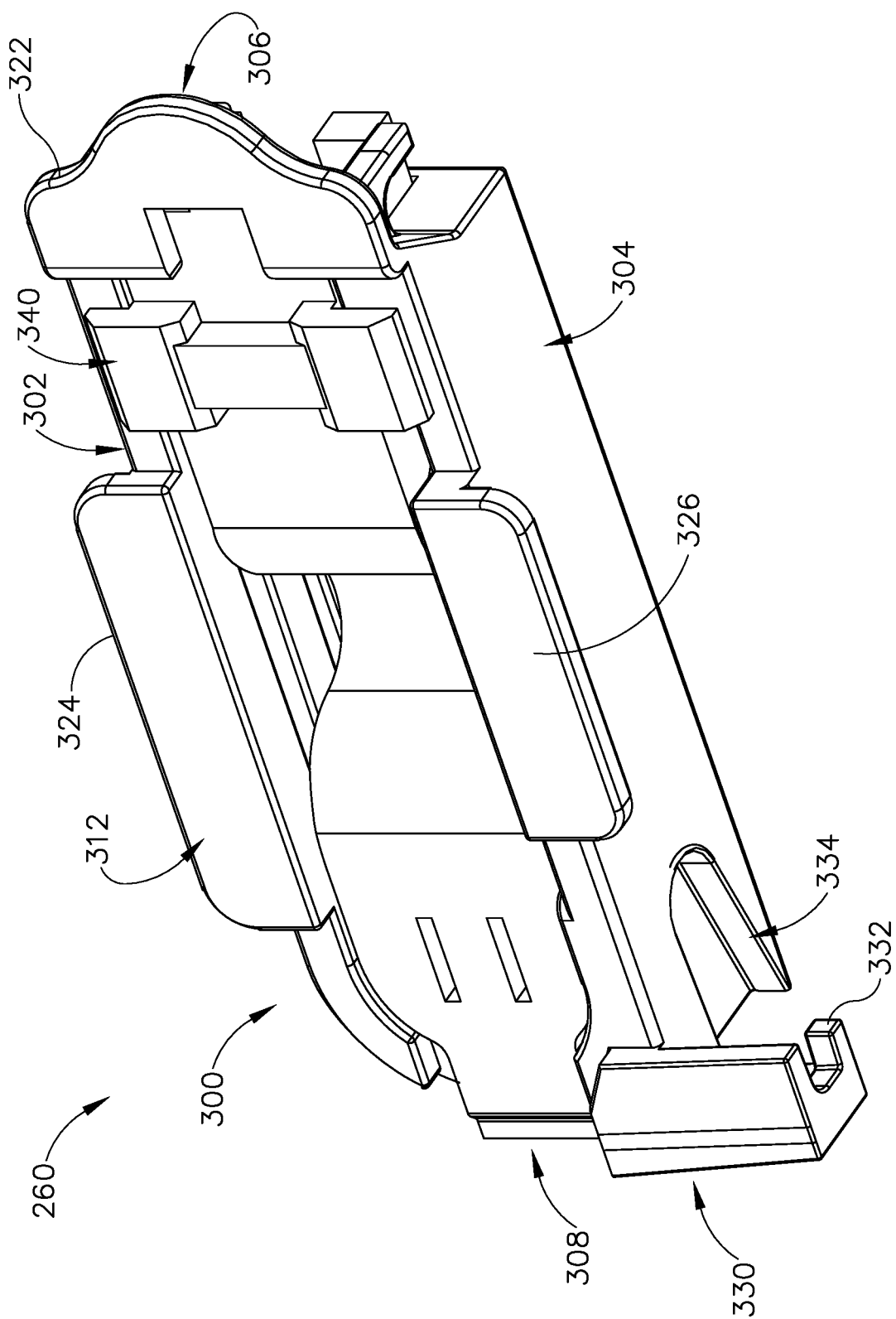
FIG. 14 depicts a rear perspective view of the staple retainer of FIG. 13.
Figure 15:
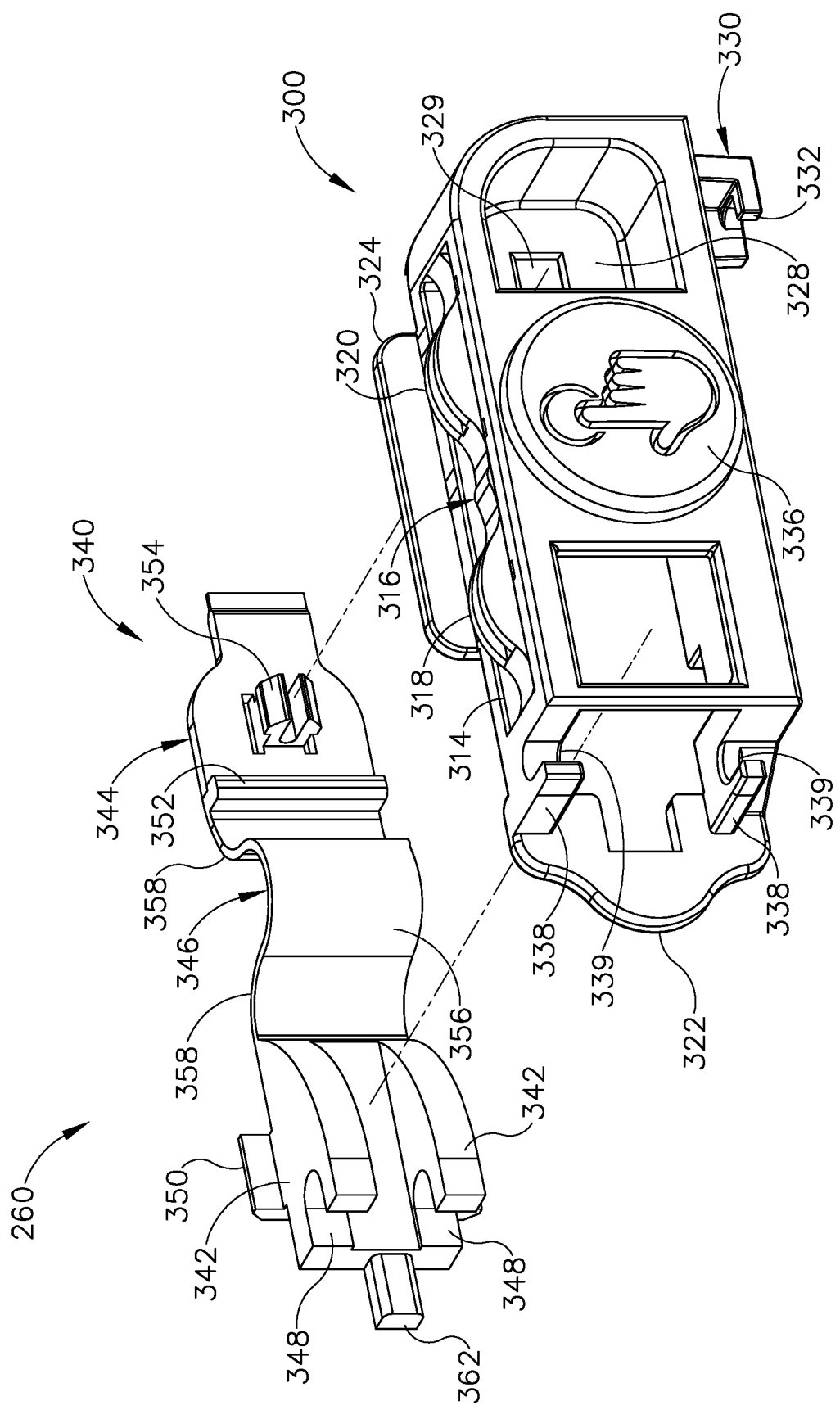
FIG. 15 depicts a disassembled front perspective view of the staple retainer of FIG. 13, showing a latch member separated from a body of the staple retainer.

As shown in FIGS. 13-15, staple retainer (260) includes a body (300) and a latch member (340) coupled with body (300). Retainer body (300) of the present version is formed with a generally rectangular shape having a first elongate body side (302), an opposed second elongate body side (304), a first body end (306), an opposed second body end (308), a front body side (310), and an opposed rear body side (312). While retainer body (300) is shown oriented in FIGS. 13-15 such that first elongate body side (302) faces upwardly and second elongate body side (304) faces downwardly, in use first elongate body side (302) may be oriented distally relative to surgical stapler (10) while second elongate body side (304) is oriented proximally, such that front and rear body sides (310, 312) face laterally relative to surgical stapler (10); for example, as shown in FIGS. 9A-9B described above and in FIGS. 17A-20D described below.

As shown best in FIGS. 13 and 15, first elongate body side (302) of retainer body (300) includes an elongate opening (314) in which a resilient contact member in the form of a resiliently deflectable beam (316) having a pair of rounded contact protrusions (318, 320) is disposed. Resilient beam (316) extends longitudinally through elongate opening (314) and is fixed at its opposed ends to adjoining portions of retainer body (300). Contact protrusions (318, 320) are disposed on and project outwardly from resilient beam (316). In the present example, each contact protrusion (318, 320) is configured with a double-wall construction along a length of resilient beam (316). While two contact protrusions (318, 320) are provided in the present version, it will be appreciated that more contact protrusions (318, 320) may be provided in other versions.

First and second contact protrusions (318, 320) are spaced apart along the length of resilient beam (316) and thus are configured to directly contact anvil plate portion (212) of staple cartridge unit (160) at respective first and second locations spaced apart along a length of anvil plate portion (212). As described in greater detail below in connection with FIGS. 17A-17B, contact protrusions (318, 320) are thus configured to cooperate to maintain anvil plate portion (212) in a parallel relationship with second elongate body side (304) and cartridge deck (164). Additionally, resilient beam (316) with contact protrusions (318, 320) are configured to resiliently deflect toward second elongate body side (304) as staple retainer (260) is coupled to staple cartridge unit (160). Advantageously, this enables staple retainer (260) to be used effectively with a variety of different types of staple cartridge units (160) each having a uniquely sized gap (G) (or "aperture") defined between cartridge deck (164) and anvil plate portion (212), such that staple retainer (260) may be implemented as a universal part within a given line of staple cartridge units (160).

As shown in FIGS. 13 and 14, retainer body (300) further includes an end flange (322) that extends outwardly from the first end of rear body side (312). Additionally, a first back plate (324) extends outwardly from the upper end of rear body side (312) in a first direction (e.g., upwardly), and a second back plate (326) extends outwardly from the lower end of rear body side (312) in a second direction (e.g., downwardly) opposite the first direction of first back plate (324). End flange (322) and back plates (324, 326) are configured to abut respective portions of a staple cartridge unit (160) and thereby cooperate to constrain staple retainer (260) in a lateral direction relative to end effector (16) of surgical stapler (10).

As also shown in FIGS. 13 and 14, retainer body (300) further includes a retention leg (330) that depends downwardly from second body end (308). A lower end of retention leg (330) includes a claw (332) that is configured to engage a slot of staple cartridge housing (162) to securely retain second body end (308) in engagement with staple cartridge housing (162), as described in greater detail below in connection with FIGS. 18-19. As best shown in FIG. 14, a tapered elongate recess (334) is formed in second elongate body side (304) at second body end). Recess (334) opens to second body end (308) and tapers in a direction toward first body end (306). Recess (334) is configured to receive a cylindrical tissue gap post (165) (see FIG. 6) projecting distally from a corresponding end of deck (164) of staple cartridge housing (162).

As best shown in FIG. 13, retainer body (300) further includes a user engagement feature in the form of a circular, button-like projection (336) that projects outwardly from a central portion of front body side (310). When staple retainer (260) is mounted to a staple cartridge unit (160), exertion of an inwardly directed force on projection (336) causes staple retainer (260) to pivot about retention leg (330), thereby driving latch member (340) to the release position to thereby permit separation of staple retainer (260) from staple cartridge unit (160), as described in greater detail below in connection with FIGS. 20A-20D. It will be appreciated that projection (336) may be alternatively shaped in other versions, and moreover that projection (336) is merely optional such that it may be omitted in some versions.

As shown best in FIG. 15, latch member (340) of staple retainer (260) of the present example is formed with a generally elongate plate-like construction and includes a pair of jaws (342) at a first end corresponding to first body end (306) of retainer body (300); an anchor portion (344) at an opposed second end corresponding to second body end (308) of retainer body (300); and an arcuate spring element (346) arranged therebetween. In the present version, arcuate spring element (346) is integrally connected with jaws (342) and anchor portion (344), such that an entirely of latch member (340) may be formed of a single material, such as a polymer. Jaws (342) are spaced apart from one along a height of latch member (340), and each jaw includes a laterally opening slot (348) configured to capture guide pin (230) of staple cartridge unit (160), as described in greater detail below. A guide plate (350) is affixed to a rear side of jaws (342) and is configured to slidably engage rear body side (312) of retainer body (300), as described below.

Figure 16A:
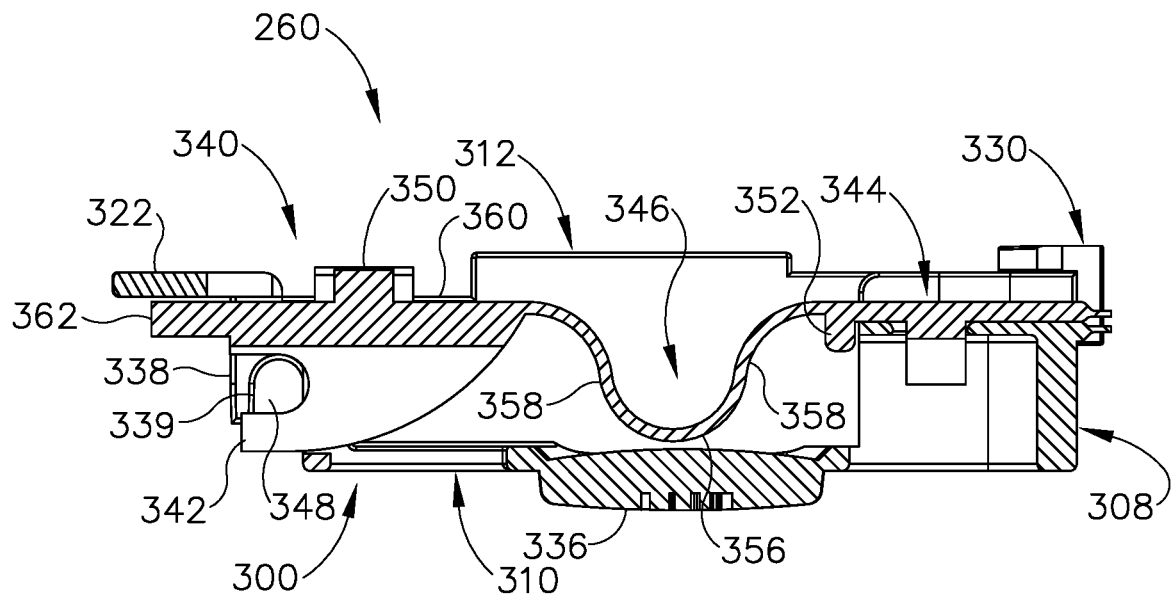
FIG. 16A depicts a top cross sectional view of the staple retainer of FIG. 13, showing the latch member in an exemplary latching position relative to the retainer body.
Figure 16B:
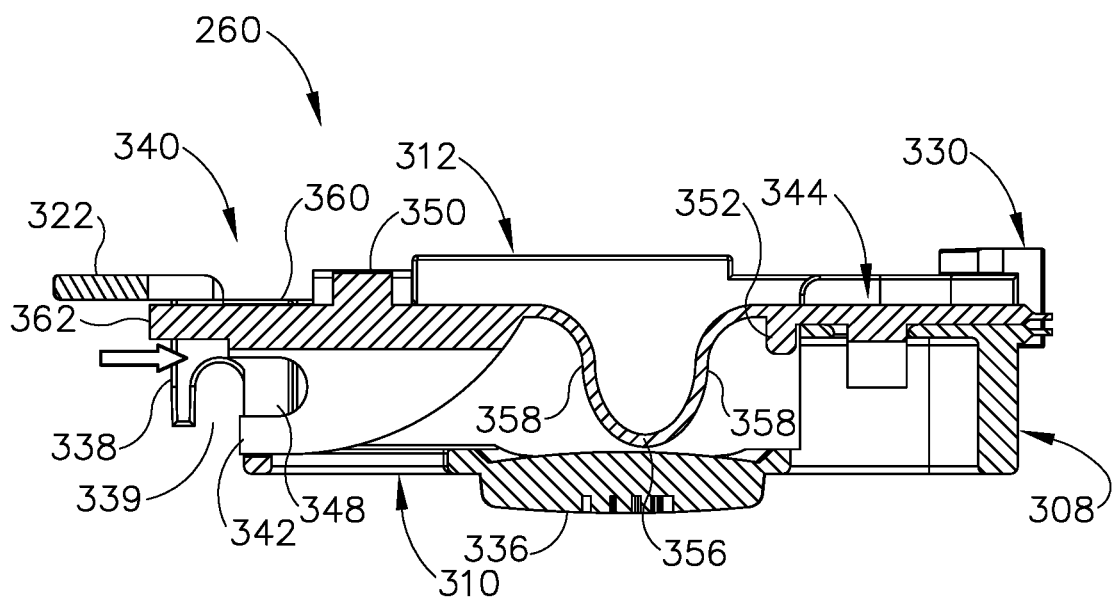
FIG. 16B depicts another top cross sectional view of the staple retainer of FIG. 13, showing the latch member in an exemplary release position relative to the retainer body.

Anchor portion (344) of latch member (340) includes a lug bar (352) that projects outwardly and extends transversely to a length of latch member (340). A snap lock element (354) is positioned adjacent to lug bar (352) in a direction toward the second end of latch member (340). Snap lock element (354) is configured to be received through a rectangular opening (329) formed in an inner plate (328) integrally disposed at second body end (308) of retainer body (300). Snap lock element (354) lockingly engages rectangular opening (329) to thereby fix anchor portion (344) of latch member (340) relative to retainer body (300). As shown in FIGS. 16A-16B, lug bar (352) is configured to abut an inner edge of inner plate (328) to thereby anchor a corresponding end of arcuate spring element (346) relative retainer body (300).

Arcuate spring element (346) of the present example has a pre-formed curvature defining a convex central portion (356) that extends toward front body side (310) of retainer body (300), and a pair of concave legs (358) that join integrally with respective inner portions of jaws (342) and anchor portion (344) of latch member (340). As shown in FIGS. 16A-16B, arcuate spring element (346) is configured to resiliently compress along a length of latch member (340) to enable jaws (342) to translate relative to anchor portion (344) between a latching position shown in FIG. 16A, and a release position shown in FIG. 16B. As shown in FIG. 16A, jaws (342) in the latching position align with a pair of hooks (338) defined at first body end (306) of retainer body (300). Each hook (338) includes a forwardly opening slot (339) that is configured to cooperate with the laterally opening slot (348) of a respective jaw (342) to capture a respective portion of guide pin (230) of staple cartridge unit (160). Thus, latch member jaws (342) and retainer body hooks (338) are configured to cooperate to capture proximal and distal portions of guide pin (230) when staple retainer (260) is mounted to staple cartridge unit (160), thereby constraining staple retainer (260) relative to staple cartridge unit (160).

As shown in FIG. 16B, arcuate spring element (346) is configured to resiliently compress to permit jaws (342) to translate inwardly toward anchor portion (344) to assume the release position. In the release position, jaws (342) release guide pin (230) from jaw slots (348) and thus permit guide pin (230) to be removed from hook slots (339) to facilitate removal of staple retainer (260) from staple cartridge unit (160). As shown, lug bar (352) anchors a corresponding leg (358) of arcuate spring element (346) to facilitate such resilient compression of arcuate spring element (346). Opposed ends of latch member guide plate (250) are slidably disposed within respective channels (360) formed in rear body side (312) of retainer body (300), and thus are configured to guide jaws (342) between the latching position (FIG. 16A) and the release position (FIG. 16B). As shown in FIG. 15, an end post (362) projects outwardly from jaws (342) at the first end of latch member (340) and extends along a longitudinal centerline of latch member (340). End post (362) is configured to be received within a corresponding notch (215) (see FIG. 7) formed in anvil coupling arm (214) when latch member (340) is in the latching position, thus further constraining staple retainer (260) relative to staple cartridge unit (160). As jaws (342) translate inwardly to the release position, end post (362) is withdrawn from notch (215) so that staple retainer (260) may be disengaged from staple cartridge unit (160).

Figure 17A:
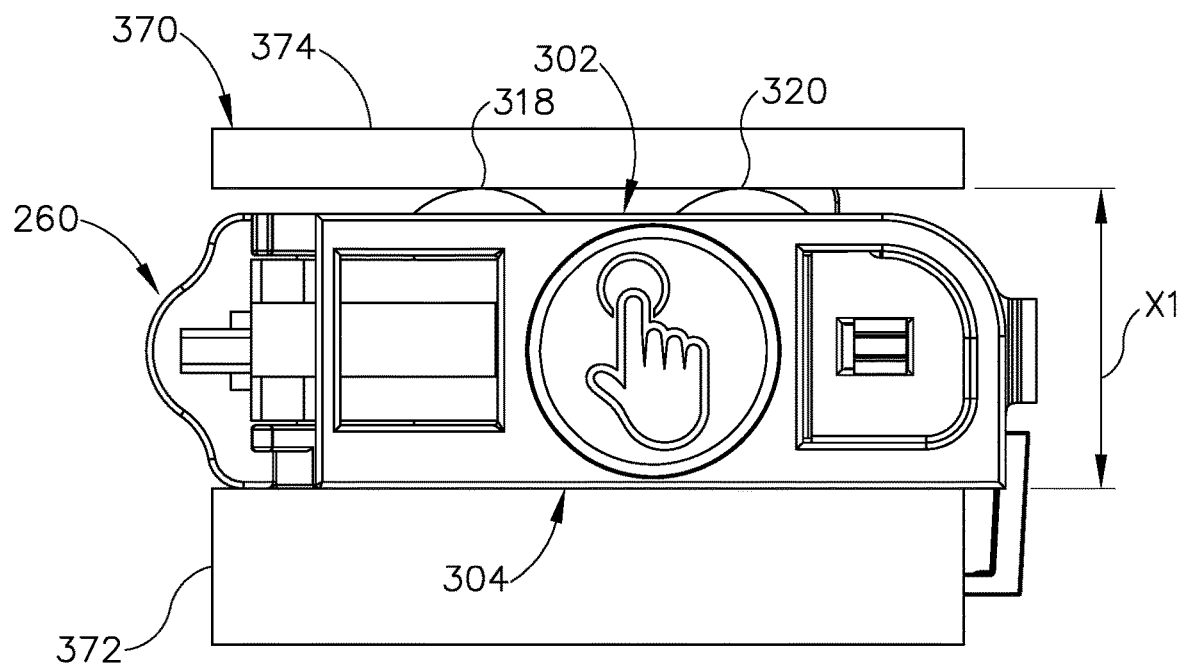
FIG. 17A depicts a schematic elevational view of the staple retainer of FIG. 13 mounted within the aperture of a first exemplary staple cartridge unit.

As briefly described above, resiliently deflectable beam (316) of retainer body (300) is configured to resiliently deflect toward second elongate body side (304) as staple retainer (260) is mounted to staple cartridge unit (160). FIG. 17A shows staple retainer (260) mounted within a first exemplary staple cartridge unit (370) having a cartridge housing (372) and an anvil plate (374) spaced apart from cartridge housing (372). Similar to cartridge housing (162) described above, cartridge housing (372) is slidable proximally and distally relative to anvil plate (374) between open and closed states. In the open state, a maximum aperture distance (X1) is defined between a deck of cartridge housing (372) and anvil plate (374). Second elongate body side (304) of retainer body (300) is configured to contact the deck of cartridge housing (372) to retain staples therein. Simultaneously, contact protrusions (318, 320) of resiliently deflectable beam (316) resiliently deflect inwardly by a first amount to contact anvil plate (374) at respective first and second locations. Contact protrusions (318, 320) thus maintain the maximum aperture distance (X1) along the full length of anvil plate (374) such that anvil plate (374) is supported parallel to the deck of cartridge housing (372) and second elongate body side (304) of retainer body (300). As a result, second elongate body side (304) is maintained in full contact with the deck of cartridge housing (162) to thereby effectively retain staples therein. Moreover, maintenance of the maximum aperture distance (X1) along the full length of anvil plate (374) facilitates proper seating of staple cartridge unit (370) within distal support structure (48) of surgical stapler (10).

Figure 17B:
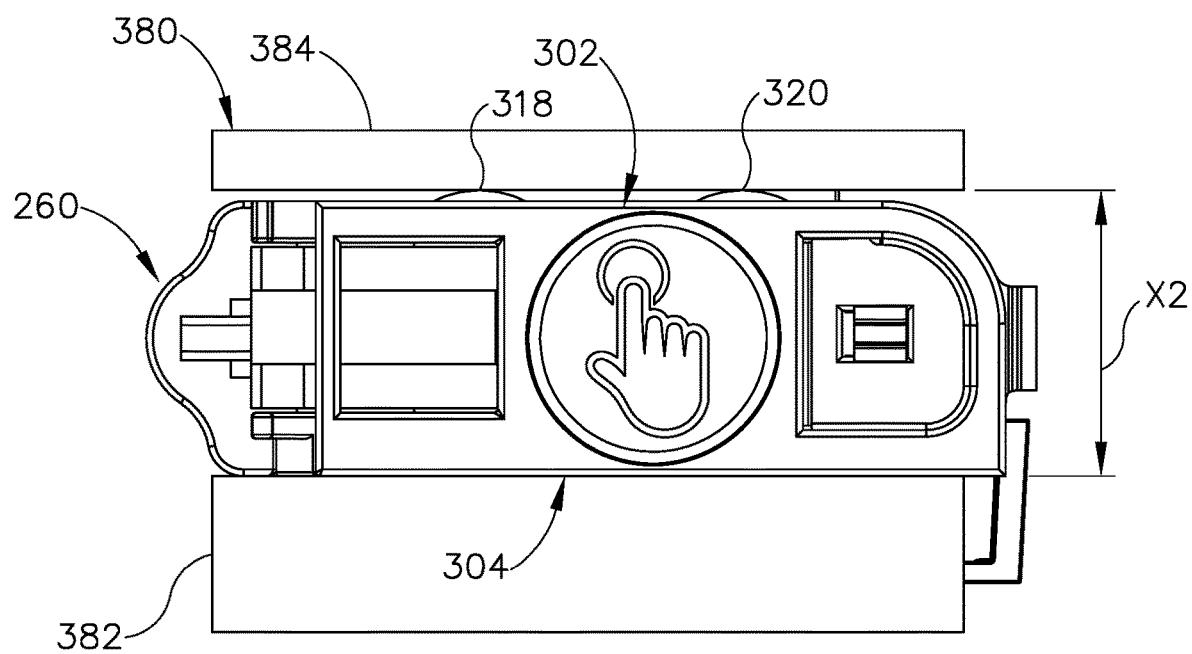
FIG. 17B depicts a schematic elevational view of the staple retainer of FIG. 13 mounted within the aperture of a second exemplary staple cartridge unit.

FIG. 17B shows staple retainer (260) mounted within a second exemplary staple cartridge unit (380) having a cartridge housing (382) and an anvil plate (384) spaced apart from cartridge housing (382). Staple cartridge unit (380) is configured to define a maximum aperture distance (X2) between cartridge housing (382) and anvil plate (384) when in a fully open state. In the present example, maximum aperture distance (X2) of second staple cartridge unit (380) is smaller than maximum aperture distance (X1) of first staple cartridge unit (370) such that staple cartridge units (370, 380) are configured for different surgical stapling applications. For instance, first staple cartridge unit (370) may be configured for stapling thicker tissues such as bronchus or colon, while second staple cartridge unit (380) may be configured for stapling thinner tissues such vascular structures. As shown in FIG. 17B, contact protrusions (318, 320) of staple retainer (260) resiliently deflect toward cartridge housing (382) to accommodate the smaller aperture distance (X2) while still supporting anvil plate (384) at first and second locations. In particular, the amount by which contact protrusions (318, 320) resiliently deflect inwardly is greater than the amount by which they deflect in connection with staple cartridge unit (370) having larger aperture distance (X1). Accordingly, contact protrusions (318, 320) maintain anvil plate (384) in parallel with the deck of cartridge housing (382), and also maintain second elongate body side (304) of retainer body (300) in full contact with the deck of cartridge housing (382) to effectively retain staples therein.

Figure 18:
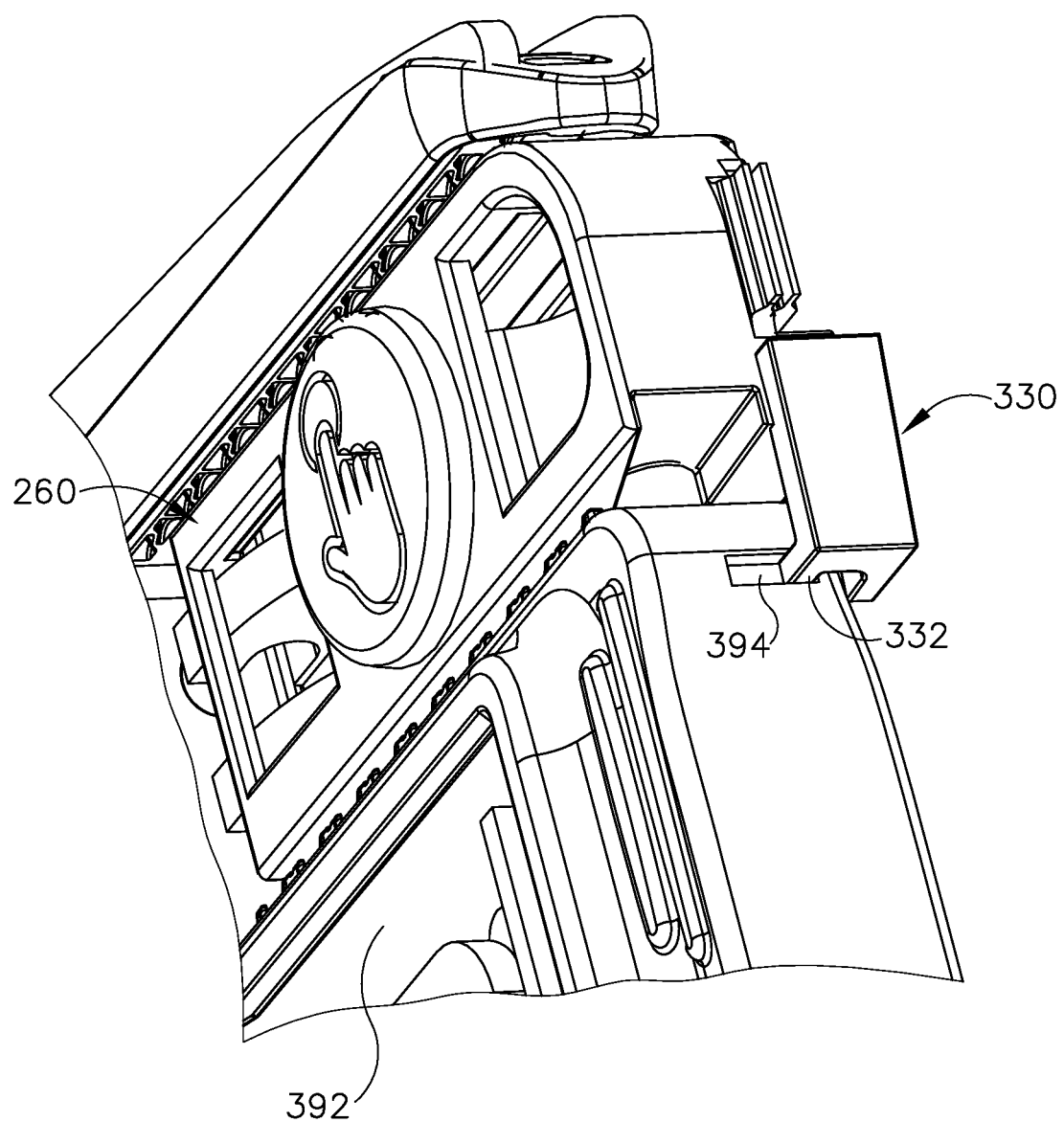
FIG. 18 depicts an enlarged perspective view of an end portion of the staple retainer of FIG. 13, showing a retention leg of the staple retainer engaged with a slot of an exemplary cartridge housing.
Figure 19:
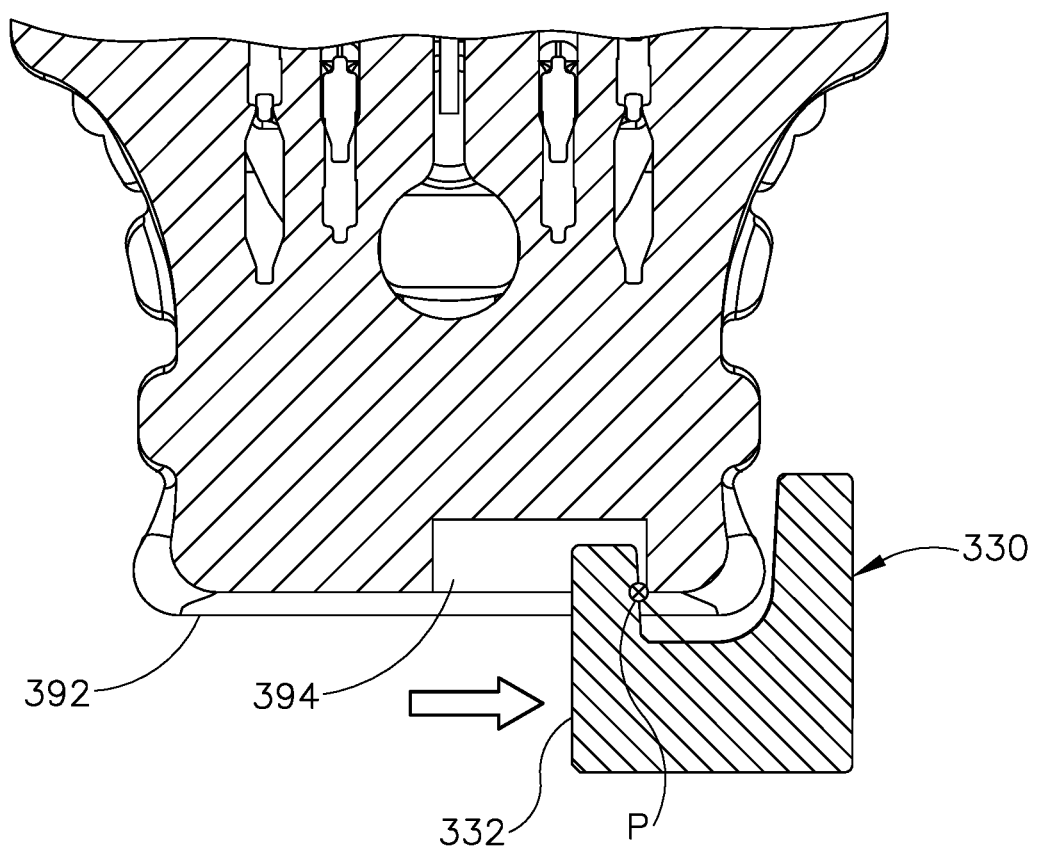
FIG. 19 depicts a top cross-sectional view of mating end portions of the staple retainer of FIG. 13 and the cartridge housing of FIG. 18, showing a pivot point defined by contact between the retention leg and an end wall of the slot.

FIGS. 18 and 19 illustrate exemplary functionality of retention leg (330) of staple retainer (260), described above. Staple retainer (260) is shown mounted to an exemplary cartridge housing (392) that is similar to cartridge housing (162) described above. As shown in FIG. 18, claw (332) of retention leg (330) is disposed within a slot (394) formed in the end of an upper body portion of cartridge housing (392). During assembly of staple retainer (260) with a staple cartridge unit, such as cartridge unit (160) described above or a cartridge unit that includes cartridge housing (392), claw (332) may first be positioned within slot (394). Then, staple retainer (260) may be pivoted about an axis defined by a point of contact between claw (332) and slot (394) to thereby engage jaws (342) of staple retainer latch member (340) with guide pin (230) to secure staple retainer (260) relative to staple cartridge unit (160). As shown in FIG. 19, such a pivot point (P) may be defined between an end wall of slot (394), and a corresponding projection of claw (332). Once staple retainer (260) is fully mounted to a staple cartridge unit (160), such as shown in FIGS. 18-19 with cartridge housing (392), retention arm claw (332) captures a corresponding portion of cartridge housing (392) to thereby constrain the corresponding end of staple retainer (260) relative to cartridge housing (392).

Figure 20A:
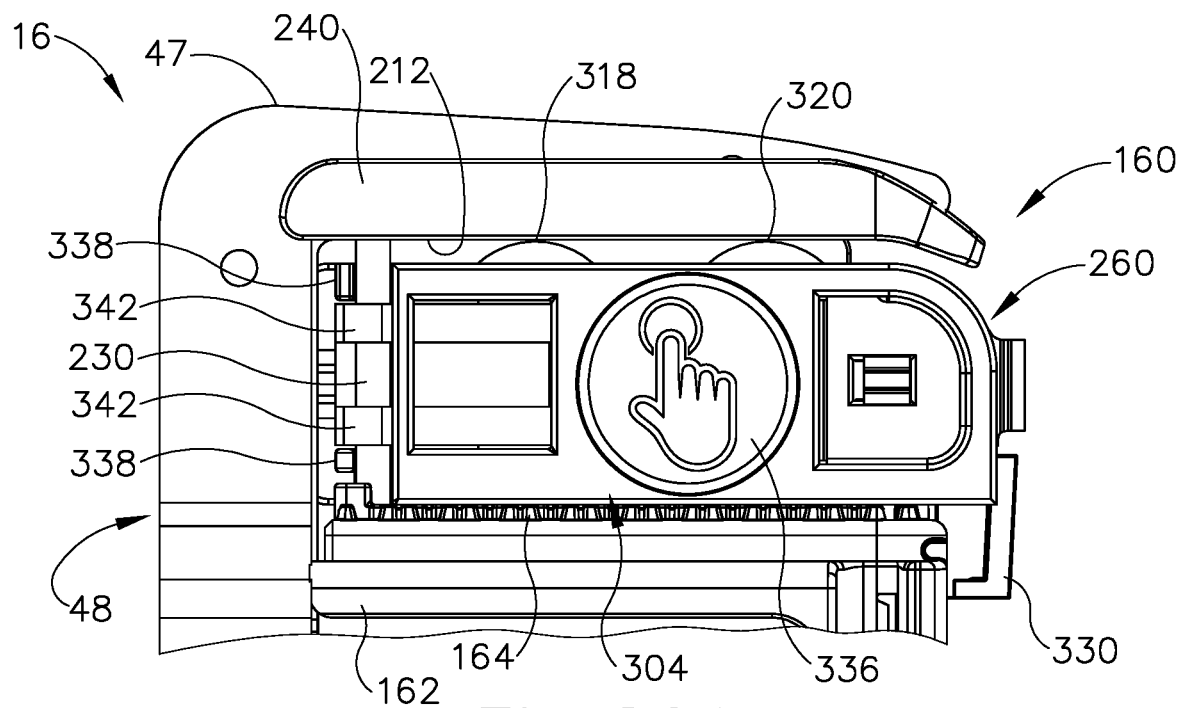
FIG. 20A depicts an enlarged side elevational view of the end effector of the surgical stapler of FIG. 1A, showing the staple retainer in a seated position in which the staple retainer retains staples within the staple cartridge unit and the latch member captures a guide pin of the staple cartridge unit.

FIGS. 20A-20D show exemplary steps for removing staple retainer (260) from staple cartridge unit (160) after staple cartridge unit (160) has been fully seated within distal support structure (48) of surgical stapler (10). FIG. 20A shows staple retainer (260) in a fully seated and latched position relative to staple cartridge unit (160) in which staple retainer (260) is positioned, between anvil plate portion (212) and cartridge deck (164). As described above, latch member jaws (342) cooperate with retainer body hooks (338) to capture guide pin (230), thereby constraining staple retainer (260) relative to staple cartridge unit (160) and securing second elongate body side (304) of staple retainer (260) in full contact with cartridge deck (164) to effectively retain staples therein. Additionally, contact protrusions (318, 320) directly and resiliently contact anvil plate portion (212) at respective first and second locations spaced apart along a longitudinal centerline of anvil plate portion (212), along elongate slot (216) (see FIG. 8). Accordingly, contact protrusions (318, 320) support anvil plate portion (212) in parallel with the cartridge deck (164), and also maintain second elongate body side (304) of retainer body (300) in full contact with cartridge deck (164) to effectively retain staples therein.

Figure 20B:
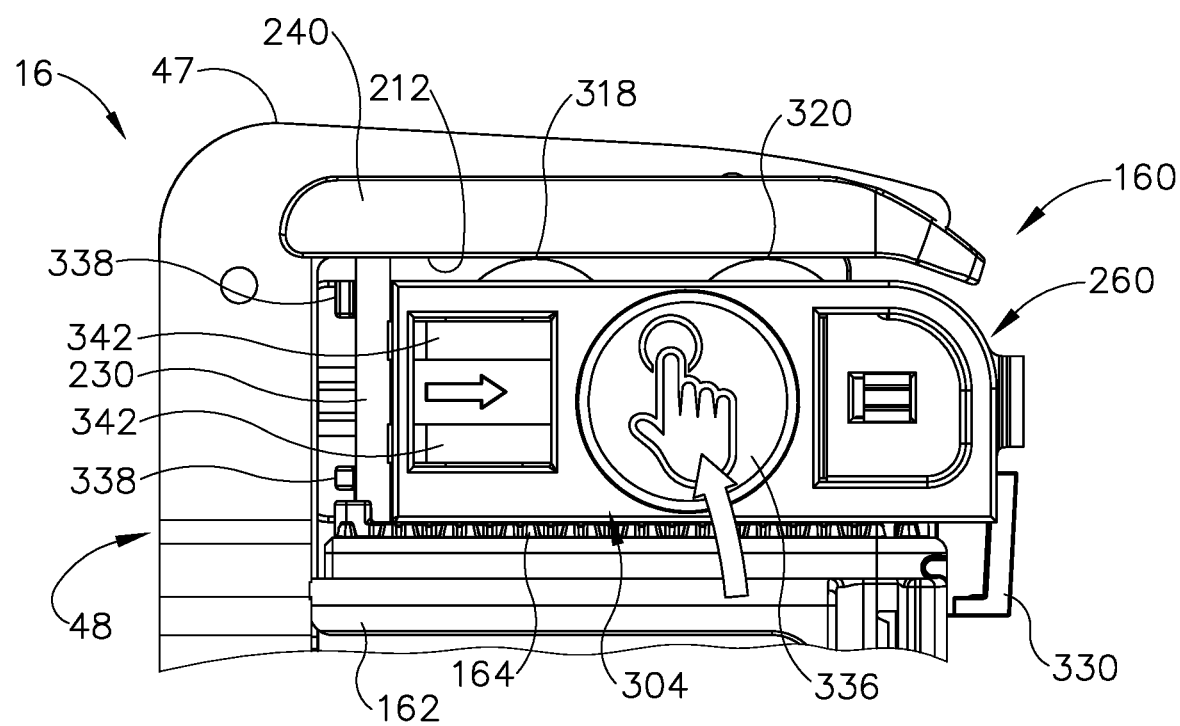
FIG. 20B depicts another enlarged side elevational view of the end effector of the surgical stapler of FIG. 1A, showing a user-applied force being exerted on a feature of the staple retainer to pivot an end of the staple retainer away from the staple cartridge unit and thereby disengage the latch member from the guide pin.
Figure 20C:
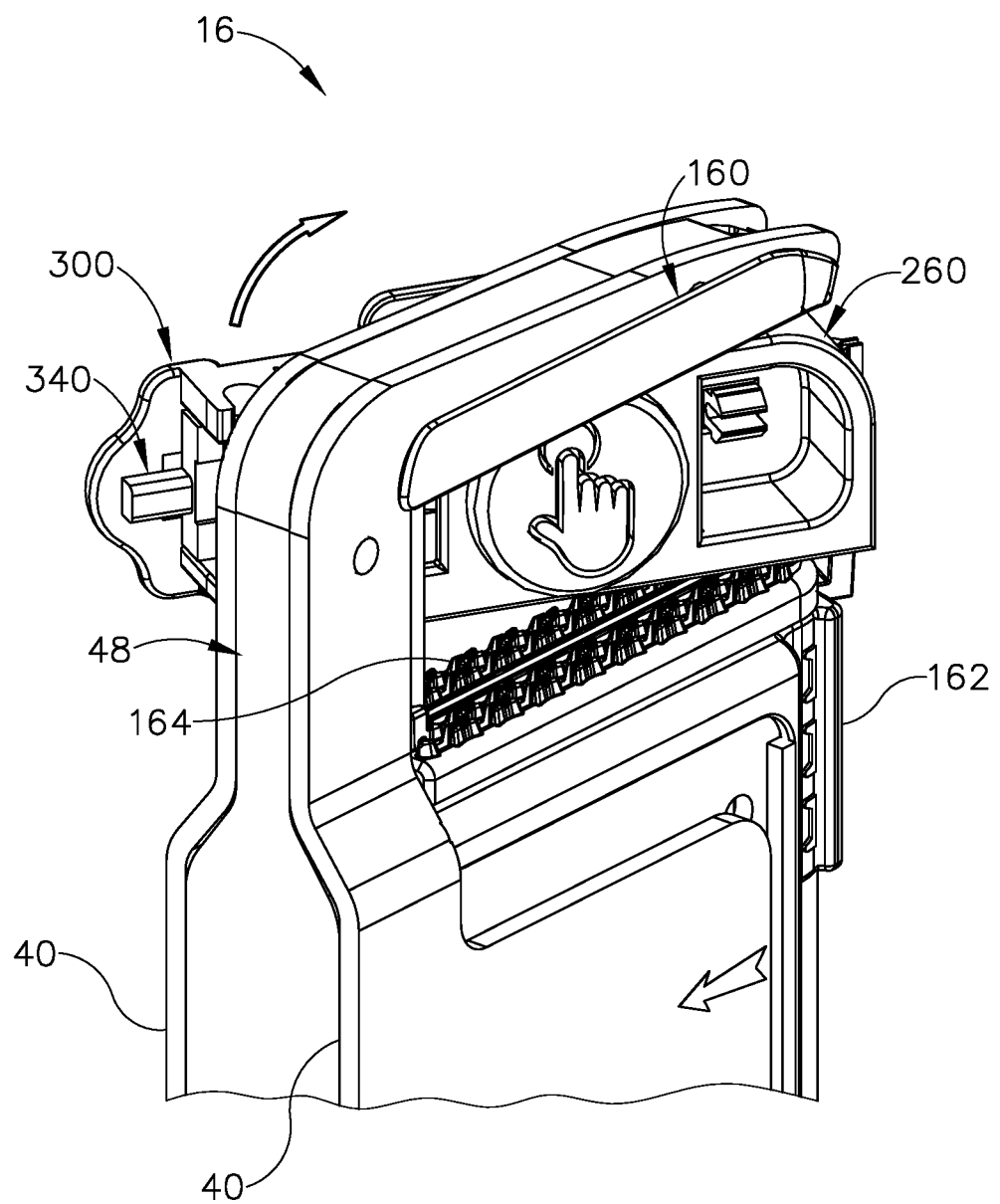
FIG. 20C depicts a perspective view of the end effector of the surgical stapler of FIG. 1A, showing the end of the staple retainer disengaged and pivoting away from the staple cartridge unit in response to the user-applied force.
Figure 20D:
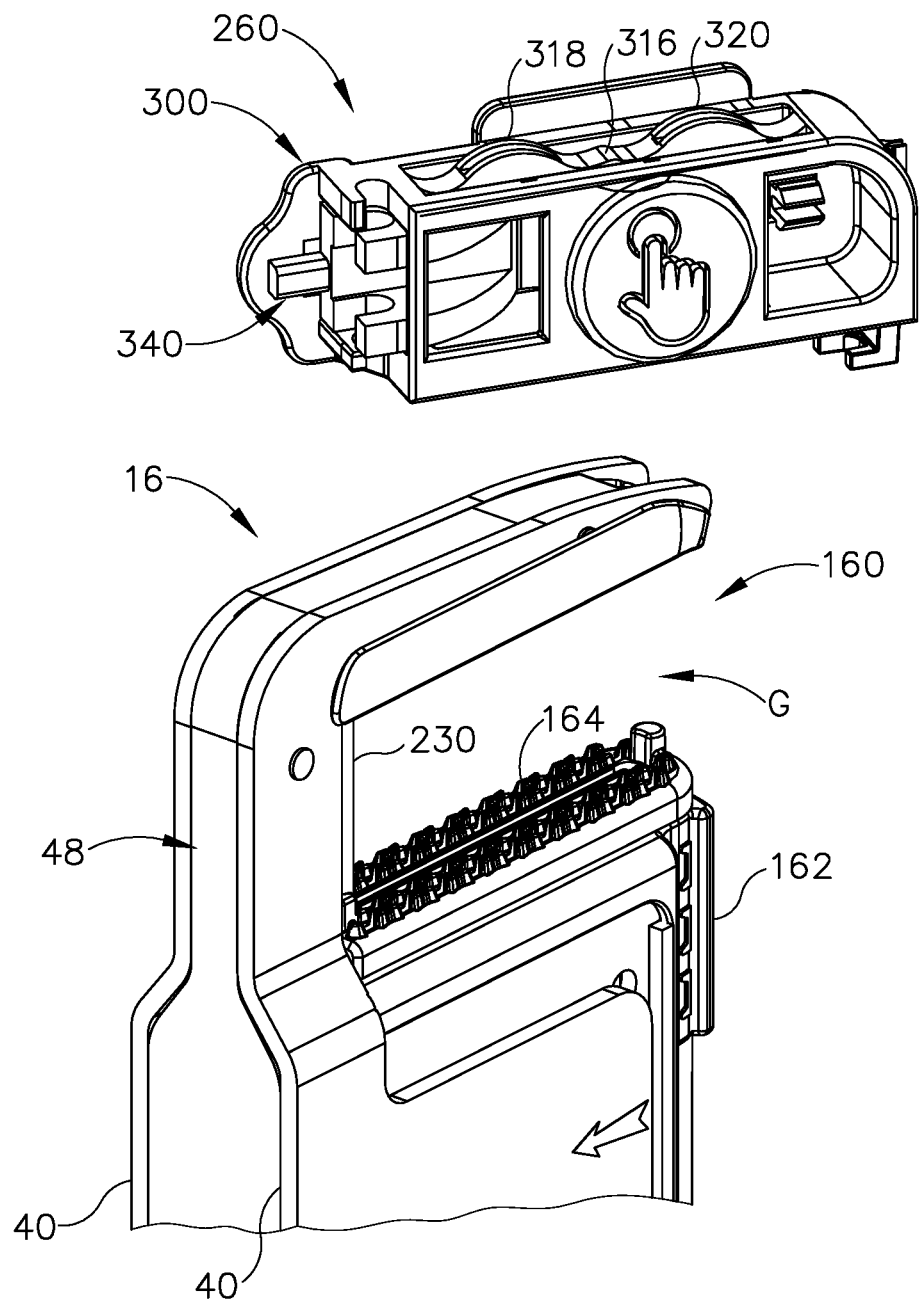
FIG. 20D depicts another perspective view of the end effector of the surgical stapler of FIG. 1A, showing the staple retainer fully removed from the staple cartridge unit.

When surgical stapler (10) is ready to be deployed within a patient to staple and cut tissue, the user stabilizes end effector (16) and pushes against button-like projection (336) of staple retainer (260), as shown in FIGS. 20B and 20C. This action forces staple retainer (260) to pivot relative to staple cartridge unit (160) about pivot point (P) defined by retention leg (330), described above. This pivoting motion forces a lateral side of guide pin (230) into contact with corresponding inner walls of staple retainer jaw slots (348). This yields a camming action that translatably drives staple retainer jaws (342) inwardly toward anchor portion (344), such that arcuate spring element (346) resiliently compresses therebetween. In this manner, latch member (340) assumes the release position that permits guide pin (230) to be released from staple retainer jaws (342) and hooks (338) as the corresponding end of staple retainer (260) pivots further away from guide pin (230), as shown in FIG. 20C. Upon full release of guide pin (230) from staple retainer (260), staple retainer (260) may be fully removed from staple cartridge unit (160), as shown in FIG. 20D. Upon separation of staple retainer (260) from staple cartridge unit (160), arcuate spring element (346) resiliently returns jaws (342) to the latching position, and resiliently deflectable beam (316) resiliently returns contact protrusions (318, 320) to a non-deflected state. Accordingly, staple retainer (260) is rendered suitable to be reattached to staple cartridge unit (160) thereafter, if desired.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A staple retainer for use with a surgical staple cartridge unit, comprising: (a) a body having a first body side and a second body side, wherein the body is configured to be positioned within an aperture defined between an anvil and a deck of the staple cartridge unit such that the first body side confronts the anvil and the second body side confronts the deck, wherein the second body side is configured to retain staples within openings formed in the deck; (b) a first protrusion disposed at the first body side, wherein the first protrusion is configured to contact the anvil at a first location; and (c) a second protrusion disposed at the first body side, wherein the second protrusion is configured to contact the anvil at a second location spaced from the first location, wherein the first and second protrusions are configured to resiliently deflect toward the second body side in response to the staple retainer being positioned within the aperture of the staple cartridge unit, wherein the first and second protrusions are configured to cooperate with the second body side to maintain a predetermined distance between the anvil and the deck.

Example 2

The staple retainer of Example 1, wherein the first and second protrusions are spaced apart along a length of the body.

Example 3

The staple retainer of any of the preceding Examples, further comprising a resiliently deflectable beam coupled to the first body side, wherein the first and second protrusions are disposed on the beam.

Example 4

The staple retainer of any of the preceding Examples, wherein the staple retainer is configured to contact the anvil along a contact plane, wherein the first and second protrusions cooperate to define the contact plane.

Example 5

The staple retainer of any of Example 4, wherein the first and second protrusions are configured to orient the anvil such that the contact plane is parallel to the second body side and the deck.

Example 6

The staple retainer of any of the preceding Examples, wherein the first and second protrusions are configured to resiliently assume a first deflected state relative to the body when the staple retainer is positioned within a first aperture of a first staple cartridge unit, wherein the first and second protrusions are configured to resiliently assume a second deflected state relative to the body when the staple retainer is positioned within a second aperture of a second staple cartridge unit, wherein the first and second apertures differ in size.

Example 7

The staple retainer of any of the preceding Examples, wherein the first body side includes an elongate opening, wherein the first and second protrusions are movably disposed within the elongate opening.

Example 8

The staple retainer of any of the preceding Examples, further comprising a latch member coupled with the body, wherein the latch member is movable relative to the body between a latching position and a release position, wherein in the latching position the latch member is configured to capture a feature of the staple cartridge unit and thereby constrain the staple retainer relative to the staple cartridge unit, wherein in the release position the latch member is configured to release the feature and thereby permit separation of the staple retainer from the staple cartridge unit.

Example 9

The staple retainer of any of Example 8, wherein the first and second protrusions are resiliently deflectable relative to the body independently of movement of the latch member relative to the body.

Example 10

The staple retainer of any of Examples 8 through 9, wherein the latch member is resiliently biased toward the latching position.

Example 11

The staple retainer of any of Examples 8 through 9, wherein a first end of the latch member is fixed relative to the body, wherein a second end of the latch member is translatable relative to the body between the latching position and the release position.

Example 12

The staple retainer of any of Examples 8 through 9, wherein the latch member includes a jaw, wherein the jaw is translatable relative to the body between the latching position and the release position.

Example 13

The staple retainer of Example 12, wherein the body includes a slot configured to receive the feature of the staple cartridge unit when the staple retainer is positioned within the aperture of the staple cartridge unit, wherein the jaw is configured to releasably capture the feature when the feature is disposed within the slot.

Example 14

A staple cartridge unit configured for use with a surgical stapler, comprising: (a) a cartridge housing having a deck that includes a plurality of openings; (b) a plurality of staples disposed within the openings; (c) an anvil having a plurality of staple forming pockets, wherein the anvil and the deck define an aperture therebetween; and (d) the staple retainer of any of the preceding Examples, wherein the staple retainer is configured to be removably positioned within the aperture such that the first and second protrusions at the first body side contact the anvil and the second body side contacts the deck.

Example 15

A surgical stapler comprising: (a) a body assembly; (b) a shaft assembly extending distally from the body assembly; and (c) an end effector at a distal end of the shaft assembly, wherein the end effector comprises: (i) a support structure, and (ii) the staple cartridge unit of claim 14 removably mounted within the support structure.

Example 16

A staple retainer for use with a surgical staple cartridge unit, comprising: (a) a body having a first body side and a second body side, wherein the body is configured to be positioned within an aperture defined between an anvil and a deck of the staple cartridge unit such that the first body side confronts the anvil and the second body side confronts the deck, wherein the second body side is configured to retain staples within openings formed in the deck; (b) a latch member coupled with the body, wherein the latch member is movable relative to the body between a latching position and a release position, wherein in the latching position the latch member is configured to capture an elongate pin of the staple cartridge unit and thereby constrain the staple retainer relative to the staple cartridge unit, wherein in the release position the latch member is configured to release the elongate pin and thereby permit separation of the staple retainer from the staple cartridge unit; and (c) a resilient contact member disposed at the first body side, wherein the resilient contact member is configured to contact the anvil and resiliently deflect toward the second body side to thereby orient the anvil parallel to the second body side and the deck.

Example 17

The staple retainer of Example 16, wherein the resilient contact member comprises a resiliently deflectable beam.

Example 18

The staple retainer of Example 17, wherein the resilient contact member further comprises a plurality of protrusions disposed on the resiliently deflectable beam, wherein the protrusions are configured to contact the anvil.

Example 19

A staple cartridge unit for use with a surgical stapler, comprising: (a) a cartridge housing, wherein the cartridge housing includes: (i) a deck, (ii) a plurality of openings formed in the deck, and (iii) a plurality of staples disposed within the openings, wherein the staples are configured to be driven from the openings and into tissue positioned against the deck; (b) an anvil movably coupled with the cartridge housing, wherein the anvil includes a plurality of pockets configured to form the staples, wherein the cartridge housing is translatable toward and away from the anvil; and (c) a staple retainer removably positioned between the deck and the anvil, wherein the staple retainer includes: (i) a body having a first body side that confronts the anvil and a second body side that confronts the deck, (ii) a first protrusion disposed at the first body side, wherein the first protrusion is configured to contact the anvil at a first location, and (iii) a second protrusion disposed at the first body side, wherein the second protrusion is configured to contact the anvil at a second location spaced from the first location, wherein at least one of the first protrusion or the second protrusion is resiliently deflectable toward the second body side.

Example 20

The staple cartridge unit of Example 19, wherein the staple cartridge unit further comprises an elongate pin that extends between the cartridge housing and the anvil, wherein the cartridge housing is configured to translate along the elongate pin toward and away from the anvil, wherein the staple retainer is configured to releasably capture the elongate pin to constrain the body relative to the cartridge housing and the anvil.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 16/395,357, entitled "Tissue Cutting Washer for Right Angle Surgical Stapler," filed on Apr. 26, 2019, publishes as U.S. Pub. 2020/0337698 on Oct. 29, 2020; U.S. patent application Ser. No. 16/395,358, entitled "Clamping Based Lockout Mechanism for Right Angle Surgical Stapler," filed on Apr. 26, 2019, published as U.S. Pub. 2020/0337699 on Oct. 29, 2020; and U.S. patent application Ser. No. 16/395,359, entitled "Cartridge Based Lockout Mechanism for Right Angle Surgical Stapler," filed on Apr. 26, 2019, published as U.S. Pub. No. 2020/0337700 on Oct. 20, 2020, the disclosures of which are incorporated by reference above.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A staple retainer for use with a surgical staple cartridge unit, comprising:
   (a) a body having a first body side and a second body side, wherein the body is configured to be positioned within an aperture defined between an anvil and a deck of the staple cartridge unit such that the first body side confronts an anvil surface of the anvil having a plurality of staple forming pockets and the second body side confronts the deck, wherein the second body side is configured to retain staples within openings formed in the deck;
   (b) a first protrusion disposed at the first body side, wherein the first protrusion is configured to contact the anvil surface at a first location; and
   (c) a second protrusion disposed at the first body side, wherein the second protrusion is configured to contact the anvil surface at a second location spaced from the first location,
   wherein the first and second protrusions are configured to resiliently deflect toward the second body side in response to the staple retainer being positioned within the aperture of the staple cartridge unit,
   wherein the first and second protrusions are configured to cooperate with the second body side to maintain a predetermined distance between the anvil and the deck.

2. The staple retainer of claim 1, wherein the first and second protrusions are spaced apart along a length of the body.

3. The staple retainer of claim 1, further comprising a resiliently deflectable beam coupled to the first body side, wherein the first and second protrusions are disposed on the beam.

4. The staple retainer of claim 1, wherein the staple retainer is configured to contact the anvil along a contact plane, wherein the first and second protrusions cooperate to define the contact plane.

5. The staple retainer of claim 4, wherein the first and second protrusions are configured to orient the anvil such that the contact plane is parallel to the second body side and the deck.

6. The staple retainer of claim 1, wherein the first and second protrusions are configured to resiliently assume a first deflected state relative to the body when the staple retainer is positioned within a first aperture of a first staple cartridge unit, wherein the first and second protrusions are configured to resiliently assume a second deflected state relative to the body when the staple retainer is positioned within a second aperture of a second staple cartridge unit, wherein the first and second apertures differ in size.

7. The staple retainer of claim 1, wherein the first body side includes an elongate opening, wherein the first and second protrusions are movably disposed within the elongate opening.

8. The staple retainer of claim 1, further comprising a latch member coupled with the body, wherein the latch member is movable relative to the body between a latching position and a release position, wherein in the latching position the latch member is configured to capture a feature of the staple cartridge unit and thereby constrain the staple retainer relative to the staple cartridge unit, wherein in the release position the latch member is configured to release the feature and thereby permit separation of the staple retainer from the staple cartridge unit.

9. The staple retainer of claim 8, wherein the first and second protrusions are resiliently deflectable relative to the body independently of movement of the latch member relative to the body.

10. The staple retainer of claim 8, wherein the latch member is resiliently biased toward the latching position.

11. A staple cartridge unit configured for use with a surgical stapler, comprising:
    (a) a cartridge housing having a deck that includes a plurality of openings;
    (b) a plurality of staples disposed within the openings;
    (c) an anvil having an anvil surface with a plurality of staple forming pockets, wherein the anvil and the deck define an aperture therebetween; and
    (d) the staple retainer of claim 1,
    wherein the staple retainer is configured to be removably positioned within the aperture such that the first and second protrusions at the first body side contact the anvil surface and the second body side contacts the deck.

12. A surgical stapler comprising:
    (a) a body assembly;
    (b) a shaft assembly extending distally from the body assembly; and
    (c) an end effector at a distal end of the shaft assembly, wherein the end effector comprises:
       (i) a support structure, and
       (ii) the staple cartridge unit of claim 11 removably mounted within the support structure.

13. The staple retainer of claim 1, wherein the first and second protrusions are interconnected.

14. The stapler retainer of claim 13, wherein the first and second protrusions are integrally connected with the body.

15. The stapler of claim 13, wherein the first and second protrusions are configured to resiliently deflect at least partially into an interior of the body.

16. The stapler of claim 13, wherein each of the first and second protrusions extends parallel to a length of the body.

17. A staple retainer for use with a surgical staple cartridge unit, comprising:
    (a) a body having a first body side and a second body side, wherein the body is configured to be positioned within an aperture defined between an anvil having an anvil surface with a plurality of staple forming pockets and a deck of the staple cartridge unit such that the first body side confronts the anvil surface and the second body side confronts the deck, wherein the second body side is configured to retain staples within openings formed in the deck;

(b) a latch member coupled with the body, wherein the latch member is movable relative to the body between a latching position and a release position, wherein in the latching position the latch member is configured to capture an elongate pin of the staple cartridge unit and thereby constrain the staple retainer relative to the staple cartridge unit, wherein in the release position the latch member is configured to release the elongate pin and thereby permit separation of the staple retainer from the staple cartridge unit; and (c) a resilient contact member disposed at the first body side, wherein the resilient contact member is configured to contact the anvil surface and resiliently deflect toward the second body side to thereby orient the anvil parallel to the second body side and the deck.

18. The staple retainer of claim 17, wherein the resilient contact member comprises a resiliently deflectable beam.

19. The staple retainer of claim 18, wherein the resilient contact member further comprises a plurality of protrusions disposed on the resiliently deflectable beam, wherein the protrusions are configured to contact the anvil surface.

20. A staple cartridge unit for use with a surgical stapler, comprising:

(a) a cartridge housing, wherein the cartridge housing includes:
   (i) a deck,
   (ii) a plurality of openings formed in the deck, and
   (iii) a plurality of staples disposed within the openings, wherein the staples are configured to be driven from the openings and into tissue positioned against the deck;

(b) an anvil movably coupled with the cartridge housing, wherein the anvil includes an anvil surface having a plurality of pockets configured to form the staples, wherein the cartridge housing is translatable toward and away from the anvil; and (c) a staple retainer removably positioned between the deck and the anvil, wherein the staple retainer includes:
   (i) a body having a first body side that confronts the anvil and a second body side that confronts the deck,
   (ii) a first protrusion disposed at the first body side, wherein the first protrusion is configured to contact the anvil surface at a first location, and
   (iii) a second protrusion disposed at the first body side, wherein the second protrusion is configured to contact the anvil surface at a second location spaced from the first location,
   wherein at least one of the first protrusion or the second protrusion is resiliently deflectable toward the second body side.

* * * * *